US012805464B2

(12) United States Patent
Pierce

(10) Patent No.: US 12,805,464 B2
(45) Date of Patent: Nov. 24, 2026

(54) CELERY CULTIVAR TBG 47

(71) Applicant: A. DUDA & SONS, INC., Oviedo, FL (US)

(72) Inventor: Lawrence K. Pierce, Quitman, AR (US)

(73) Assignee: A. Duda & Sons, Inc., Oviedo, FL (US)

(*) Notice: Subject to any disclaimer, the term of this patent is extended or adjusted under 35 U.S.C. 154(b) by 334 days.

(21) Appl. No.: 18/411,831

(22) Filed: Jan. 12, 2024

(65) Prior Publication Data

US 2025/0228175 A1 Jul. 17, 2025

(51) Int. Cl.
*A01H 6/06* (2018.01)
*A01H 5/04* (2018.01)

(52) U.S. Cl.
CPC ............... *A01H 6/064* (2018.05); *A01H 5/04* (2013.01)

(58) Field of Classification Search
CPC ...................................................... A01H 6/064
See application file for complete search history.

(56) References Cited

U.S. PATENT DOCUMENTS

| | | | |
|---|---|---|---|
| 5,124,505 A | 6/1992 | Orton et al. | |
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,850,009 A | 12/1998 | Kevern | |
| 6,812,385 B2 | 11/2004 | Pierce | |
| 6,822,143 B2 | 11/2004 | Pierce | |
| 7,193,142 B2 | 3/2007 | Trammell et al. | |
| 7,351,883 B2 | 4/2008 | Pierce et al. | |
| 7,365,248 B2 | 4/2008 | Pierce | |
| 8,524,993 B2 | 9/2013 | Pierce | |
| 8,598,424 B2 | 12/2013 | Pierce | |
| 8,598,425 B2 | 12/2013 | Pierce | |
| 9,433,162 B2 | 9/2016 | Pierce | |
| 9,439,374 B2 | 9/2016 | Pierce | |
| 9,706,725 B1 * | 7/2017 | Pierce | A01H 6/064 |
| 9,713,308 B2 | 7/2017 | Pierce | |
| 10,306,857 B1 | 6/2019 | Pierce | |
| 10,440,913 B2 | 10/2019 | Pierce | |
| 12,557,749 B2 * | 2/2026 | Pierce | A01H 6/064 |

OTHER PUBLICATIONS

Haun et al Plant Physiology vol. 155, pp. 645-655 (Year: 2011).*
Großkinsky et al Journal of Experimental Botany vol. 66, No. 11, pp. 5429-5440 (Year: 2015).*
PVP 9800117 To: A. Duda & Sons, Inc. For: Gene's Gem 12 (celery) issued Jun. 14, 2001 (Year: 2001).*
Allard, R.W., 1999, Breeding Self-Pollinated Plants, Principles of Plant Breeding, 2nd ed., John Wiley & Sons, Inc., pp. 175-197.
Altpeter, F., et al., 2016, Advancing Crop Transformation in the Era of Genome Editing, *The Plant Cell*, 28:1510-1520.
Bennetzen, et al., 1992, Approaches and progress in the molecular cloning of plant disease resistance genes, *Genetic Engineering*, 14:99-124.
Browers & Orton, "Biotechnology in Agriculture and Forestry", vol. 2: Crops 1, Ed. Y.P.S Bajaj, Springer-Verlag, Berlin, Heidelberg, 1986, pp. 405-420.
DeBolle, et al., 1996, Antimicrobial peptides from *Mirabilis jalapa* and *Amaranthus caudatus*: expression, processing, localization and biological activity in transgenic tobacco, *Plant Molec. Biol.*, 31:993-1008.
Epstein L, Kaur S, Henry PM. The Emergence of *Fusarium oxysporum* f. sp. *apii* Race 4 and *Fusarium oxysporum* f. sp. *coriandril* Highlights Major Obstacles Facing Agricultural Production in Coastal California in a Warming Climate: A Case Study. Front Plant Sci. Jun. 13, 2022;13:921516. doi: 10.3389/fpls.2022.921516. PMID: 35769302; PMCID: PMC9234665.
Eshed, et al., 1996, Less-than-additive epistatic interactions of quantitative trait loci in tomato, *Genetic*, 143:1807-1817.
Hessayon, D.G., "The Vegetable & Herb Expert", 2003, pp. 47-49.
Jiang, G.L., "Molecular Markers and Marker-Assisted Breeding in Plants", Plant Breeding from Laboratories to Fields, InTech, 2013, pp. 45-83.
Kamburova, V.S., et al., "Genome Editing in Plants: An Overview of Tools and Applications", *Intl J. of Agronomy*, 2017, Article ID 7315351, 15 pages.
Kaur S, Barakat R, Kaur J, Epstein L. The Effect of Temperature on Disease Severity and Growth of *Fusarium oxysporum* f. sp. *apii* Races 2 and 4 in Celery. Phytopathology. Feb. 2022;112(2):364-372. doi: 10.1094/PHYTO-11-20-0519-R. Epub Feb. 1, 2022. PMID: 34152209.
Kraft, T., Hansen, M., and Nilsson, N.O., "Linkage disequilibrium and fingerprinting in sugar beet", *Theor. Appl. Genet.*, 2000, 101:323-326.
Malzahn, A., et al., "Plant genome editing with TALEN and CRISPR", *Cell Biosci*, 2017, 7:21, 18 pages.

(Continued)

*Primary Examiner* — David H Kruse
(74) *Attorney, Agent, or Firm* — Klarquist Sparkman, LLP

(57) ABSTRACT

A celery cultivar designated TBG 47 is disclosed. The invention relates to the seeds of celery cultivar TBG 47, to the plants of celery cultivar TBG 47, and to methods for producing a celery plant by crossing the cultivar TBG 47 with itself or another celery cultivar. The invention further relates to methods for producing a celery plant containing in its genetic material one or more transgenes and to the transgenic celery plants and plant parts produced by those methods. This invention also relates to celery cultivars or breeding cultivars and plant parts derived from celery cultivar TBG 47, to methods for producing other celery cultivars, lines or plant parts derived from celery cultivar TBG 47, and to the celery plants, varieties, and their parts derived from the use of those methods. The invention further relates to hybrid celery seeds, plants, and plant parts produced by crossing cultivar TBG 47 with another celery cultivar.

24 Claims, No Drawings

(56) References Cited

OTHER PUBLICATIONS

McCarthy, et al., 2001, Commercial celery production in eastern North Carolina, Horticulture Information Leaflet 27, NC State University.
Pang, S., et al., "Expression of a gene encoding a scorpion insectotoxin peptide in yeast, bacteria and plants", *Gene*, 1992, 116:165-172.
Quiros, et al., "Use of stem proteins and isozymes for the identification of celery varieties", *Plant Cell Reports*, 1987, 6:114-117.
U.S. Plant Variety Protection Cert. No. 200200021, issued Apr. 29, 2003, 36 pages.
U.S. Plant Variety Protection Cert. No. 200400326, issued Jun. 15, 2005, 16 pages.
U.S. Plant Variety Protection certificate No. 9500019, issued Dec. 29, 1995, 25 pages.
U.S. Plant Variety Protection Certificate No. 9900063, issued Sep. 12, 2001, 19 pages.
Waycott, W. and Fort, S.B., "Differentiation of nearly identical germplasm accessions by a combination of molecular and morphologic analyses", *Genome*, 1994, 37(4):577-583.

* cited by examiner

CELERY CULTIVAR TBG 47

BACKGROUND OF THE INVENTION

The present invention relates to a new and distinctive celery (*Apium graveolens* var. *dulce*) variety designated TBG 47. All publications cited in this application are herein incorporated by reference.

There are numerous steps in the development of any novel, desirable plant germplasm. Plant breeding begins with the analysis, definition of problems and weaknesses of the current germplasm, the establishment of program goals, and the definition of specific breeding objectives. The next step is selection of germplasm that possesses the traits to meet the program goals. The goal is to combine in a single variety or hybrid an improved combination of desirable traits from the parental germplasm. These important traits may include improved flavor, increased stalk size and weight, higher seed yield, improved color, resistance to diseases and insects, tolerance to drought and heat, and better agronomic quality.

All cultivated forms of celery belong to the species *Apium graveolens* var. *dulce* that is grown for its edible stalk. As a crop, celery is grown commercially wherever environmental conditions permit the production of an economically viable yield. In the United States, the principal growing regions are California, Florida, Arizona, and Michigan. Fresh celery is available in the United States year-round, although the greatest supply is from November through January. For planting purposes, the celery season is typically divided into two seasons: summer and winter, with Florida and the southern California areas harvesting from November to July, and Michigan and northern California harvesting from July to October. Celery is consumed as fresh, raw product and as a cooked vegetable.

Celery is a cool-season biennial that grows best from 60° F. to 65° F. (16° C. to 18° C.) but will tolerate temperatures from 45° F. to 75° F. (7° C. to 24° C.). Freezing damages mature celery by splitting the petioles or causing the skin to peel, making the stalks unmarketable. This can be a problem for crops planted in the winter regions; however, celery can tolerate minor freezes early in the production cycle.

The two main growing regions for celery in California are located along the Pacific Ocean: the central coast or summer production area (Monterey, San Benito, Santa Cruz, and San Luis Obispo Counties) and the south coast or winter production area (Ventura and Santa Barbara Counties). A minor region (winter) is located in the southern deserts (Riverside and Imperial Counties).

In the south coast, celery is transplanted from early August to April for harvest from November to mid-July; in the Santa Maria area, celery is transplanted from January to August for harvest from April through December. In the central coast, fields are transplanted from March to September for harvest from late June to late December. In the southern deserts, fields are transplanted in late August for harvest in January.

Commonly used celery varieties for coastal production include Command, Mission, Conquistador and Sonora. Some shippers use their own proprietary varieties. Celery seed is very small and difficult to germinate. All commercial celery is planted as greenhouse-grown transplants. Celery grown from transplants is more uniform than from seed and takes less time to grow the crop in the field. Transplanted celery is traditionally placed in double rows on 40-inch (100-cm) beds with plants spaced between 6.0 and 7.0 inches apart.

Celery requires a relatively long and cool growing season (*The physiology of vegetable crops* by Pressman, CAB Intl., New York, 1997). Earlier transplanting results in a longer growing season, increased yields, and better prices. However, celery scheduled for spring harvest often involves production in the coolest weather conditions of winter, a period during which vernalization can occur. If adequate vernalization occurs for the variety, bolting may be initiated. Bolting is the premature rapid elongation of the main celery stem into a floral axis (i.e., during the first year for this normally biennial species). Bolting slows growth as the plant approaches marketable size and leaves a stalk with no commercial value. Different varieties have different vernalization requirements, but in the presence of bolting, the length of the seed stem can be used as a means of measuring bolting tolerance that exists in each different variety. The most susceptible varieties reach their vernalization requirement earlier and have time to develop the longest seed stems, while the moderately tolerant varieties take longer to reach their vernalization requirement and have less time to develop a seed stem which would therefore be shorter. Under normal production conditions, the most tolerant varieties may not achieve their vernalization requirement and therefore not produce a measurable seed stem.

The coldest months when celery is grown in the United States are December, January, and February. If celery is going to reach its vernalization requirements to cause bolting, it is generally younger celery that is exposed to this cold weather window. This celery generally matures in the months of April and May which constitute what the celery industry calls the bolting or seeder window. The bolting or seeder window is a period where seed stems are generally going to impact the quality of the marketable celery, and this is most consistently experienced in celery grown in the Southern California region. The presence of seed stems in celery can be considered a major marketable defect as set forth in the USDA grade standards. If the seed stem is longer than twice the diameter of the celery stalk or eight inches, the celery no longer meets the standards of US Grade #1. If the seed stem is longer than three times the diameter of the celery stalk, the celery is no longer marketable as US Grade #2 (*United States Standards for Grades of Celery*, United States Department of Agriculture, reprinted January 1997).

Celery is an allogamous biennial crop. The celery genome consists of 11 chromosomes. Its high degree of out-crossing is accomplished by insects and wind pollination. Pollinators of celery flowers include a large number of wasp, bee, and fly species. Celery is subject to inbreeding depression, which appears to be dependent upon the genetic background as some lines are able to withstand selfing for three or four generations.

Celery flowers are protandrous, with pollen being released 3-6 days before stigma receptivity. At the time of stigma receptivity, the stamens will have fallen, and the two stigmata will have unfolded in an upright position. The degree of protandry varies, which makes it difficult to perform reliable hybridization, due to the possibility of accidental selfing.

Celery flowers are very small, which significantly hinders easy removal of individual anthers. Furthermore, different developmental stages of the flowers in umbels make it difficult to avoid uncontrolled pollinations. The standard hybridization technique in celery consists of selecting flower buds of the same size and eliminating the older and younger flowers. Then, the umbellets are covered with glycine paper bags for a 5 to 10-day period, during which the stigmas become receptive. At the time the flowers are receptive, available pollen or umbellets shedding pollen from selected male parents are rubbed on to the stigmas of the female parent.

Celery plants require a period of vernalization while in the vegetative phase in order to induce seed stalk development. A period of 6-10 weeks at 5° C. to 8° C. when the plants are greater than 4 weeks old is usually adequate for most non-bolting tolerant varieties. Due to a wide range of responses to the cold treatment, it is often difficult to synchronize crossing, since plants will flower at different times. However, pollen can be stored for 6-8 months at −10° C. in the presence of silica gel or calcium chloride with a viability decline of only 20-40%, thus providing flexibility to perform crosses over a longer time.

For selfing, the plant or selected umbels are caged in cloth bags. These are shaken several times during the day to promote pollen release. Houseflies (*Musca domestica*) can also be introduced weekly into the bags to perform pollinations.

Celery in general is an important and valuable vegetable crop. Thus, a continuing goal of celery plant breeders is to develop stable, high yielding celery cultivars that are resistant to diseases and agronomically sound to maximize the amount of yield produced on the land. To accomplish this goal, the celery breeder must select and develop celery plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a novel celery cultivar designated TBG 47. Also provided are celery plants having the physiological and morphological characteristics of celery cultivar TBG 47. This invention thus relates to the seeds of celery cultivar TBG 47, to the plants of celery cultivar TBG 47, and to methods for producing a celery plant by crossing celery TBG 47 with itself or another celery plant, to methods for producing a celery plant containing in its genetic material one or more transgenes and to the transgenic celery plants produced by that method. This invention also relates to methods for producing other celery cultivars derived from celery cultivar TBG 47 and to the celery cultivar derived by the use of those methods. This invention further relates to hybrid celery seeds and plants produced by crossing celery cultivar TBG 47 with another celery line.

This invention further relates to the $F_1$ hybrid celery plants and plant parts grown from the hybrid seed produced by crossing celery cultivar TBG 47 to a second celery plant. Still further included in the invention are the seeds of an $F_1$ hybrid plant produced with the celery cultivar TBG 47 as one parent, the second generation ($F_2$) hybrid celery plant grown from the seed of the $F_1$ hybrid plant, and the seeds of the $F_2$ hybrid plant. Thus, any such methods using the celery cultivar TBG 47 are part of this invention: selfing, backcrosses, hybrid production, crosses to populations, and the like. All plants produced using celery cultivar TBG 47 as at least one parent are within the scope of this invention. Advantageously, the celery cultivar could be used in crosses with other, different, celery plants to produce first generation ($F_1$) celery hybrid seeds and plants with superior characteristics.

The invention further provides methods for developing celery plants derived from celery cultivar TBG 47 in a celery plant breeding program using plant breeding techniques including recurrent selection, backcrossing, pedigree breeding, restriction fragment length polymorphism enhanced selection, genetic marker enhanced selection and transformation. Seeds, celery plants, and parts thereof, produced by such breeding methods are also part of the invention.

In another aspect, the present invention provides protoplasts and regenerable cells for use in tissue culture of celery cultivar TBG 47. The tissue culture will preferably be capable of regenerating plants having essentially all of the physiological and morphological characteristics of the foregoing celery plant, and of regenerating plants having substantially the same genotype as the foregoing celery plant. Preferably, the regenerable cells in such tissue cultures will be callus, protoplasts, meristematic cells, leaves, pollen, embryos, roots, root tips, anthers, pistils, flowers, seeds, petioles, and suckers. Still further, the present invention provides celery plants regenerated from the tissue cultures of the invention.

In another aspect, the present invention provides for single or multiple gene converted plants of TBG 47. The single or multiple transferred gene(s) may preferably be a dominant or recessive allele. Preferably, the single or multiple transferred gene(s) will confer such traits as male sterility, herbicide resistance, insect resistance, modified fatty acid metabolism, modified carbohydrate metabolism, resistance for bacterial, fungal, or viral disease, male fertility, enhanced nutritional quality and industrial usage or the transferred gene will have no apparent value except for the purpose of being a marker for variety identification. The single or multiple gene(s) may be a naturally occurring celery gene or a transgene introduced through genetic engineering techniques.

The invention also relates to methods for producing a celery plant containing in its genetic material one or more transgenes and to the transgenic celery plant produced by those methods.

In another aspect, the present invention provides for methods of introducing one or more desired trait(s) into celery cultivar TBG 47 and plants or seeds obtained from such methods. The desired trait(s) may be, but not exclusively, a single gene, preferably a dominant but also a recessive allele. Preferably, the transferred gene or genes will confer such traits as male sterility, herbicide resistance, insect resistance, disease resistance, resistance for bacterial, fungal, or viral disease, male fertility, water stress tolerance, enhanced nutritional quality, modified fatty acid metabolism, modified carbohydrate metabolism, enhanced plant quality, and industrial usage. The gene or genes may be naturally occurring rice gene(s). The method for introducing the desired trait(s) may be a backcrossing process making use of a series of backcrosses to the celery cultivar TBG 47 during which the desired trait(s) is maintained by selection. The desired trait may also be introduced via transformation.

The invention further relates to methods for genetically modifying a celery plant of the celery cultivar TBG 47 and to the modified celery plant produced by those methods. The genetic modification methods may include, but are not limited to mutation, genome editing, gene silencing, RNA interference, backcross conversion, genetic transformation, single and multiple gene conversion, and/or direct gene transfer. The invention further relates to a genetically modified celery plant produced by the above methods, wherein the genetically modified celery plant comprises the genetic modification and otherwise comprises all of the physiological and morphological characteristics of celery cultivar TBG 47.

In addition to the exemplary aspects and embodiments described above, further aspects and embodiments will become apparent by reference by the study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Allele. An allele is any of one or more alternative form of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first-generation hybrid $F_1$ with one of the parental genotype of the $F_1$ hybrid.

Bacterial blight. A bacterial disease of celery caused by *Pseudomonas syringae* pv. *apii*. The initial symptoms appear on the leaves as small, bright yellow, circular spots. As these enlarge with a yellow halo, they turn to a rust color. As the spots increase in number, they merge to eventually kill the leaf tissue. Bacterial blight is favored by cool, wet conditions and at least 10 hours of leaf wetness is required for infection. The disease is spread by water splashes, farm machinery and field workers especially when the foliage is wet.

Black streak. A physiological disorder in celery plants causing some petioles, when cut, to show "black streaks" in the lower half or throughout the entire length of the petiole, making the entire crop unmarketable. Symptoms can be triggered under field conditions by high temperatures.

Blackheart. Blackheart is due to a lack of movement of sufficient calcium that causes the plant to turn brown and begin to decay at the growing point of the plant. Celery in certain conditions, such as warm weather, grows very rapidly and is incapable of moving sufficient amounts of calcium to the growing point.

Bolting. The premature development of a flowering or seed stalk, and subsequent seed, before a plant produces a food crop. Bolting is typically caused by late planting when temperatures are low enough to cause vernalization of the plants.

Bolting period. Also known as the bolting or seeder window, and generally occurs in celery that is transplanted from the middle of December through January and matures in April to May. The intensity and actual weeks that bolting may be observed vary from year to year, but it is generally observed in this window.

Bolting tolerance. The amount of vernalization that is required for different celery varieties to bolt is genetically controlled. Varieties with increased tolerance to bolting require greater periods of vernalization in order to initiate bolting. A comparison of bolting tolerance between varieties can be measured by the length of the flowering or seed stem under similar vernalization conditions.

Brown stem. A disease caused by the bacterium *Pseudomonas cichorii* that causes petiole necrosis. Brown Stem is characterized by a firm, brown discoloration throughout the petiole.

Celeriac or Root celery (*Apium graveolens* L. var. *rapaceum*). A plant that is related to celery but instead of having a thickened and succulent leaf petiole as in celery, celeriac has an enlarged hypocotyl and upper root that is the edible product.

Celery heart. The center-most interior petioles and leaves of the celery stalk. They are not only the smallest petioles in the stalk, but the youngest as well. Some varieties are considered heartless because they go right from very large petioles to only a couple of very small petioles. The heart is comprised of the petioles that are closest to the meristem of the celery stalk.

*Colletotrichum*. One of the most common and important genera of plant-pathogenic fungi. Causes post-harvest rots, and anthracnose spots and blights of aerial plant parts. In celery it is also frequently accompanied by curling of the foliage and black heart. *Colletotrichum acutatum* sensu lato has been reclassified to be *Colletotrichum fioriniae* (Pavel, J. A., The Etiology, Virulence, and Phylogenetics of the Celery Anthracnose Pathogen, *Colletotrichum fioriniae* (=*C. acutatum* sensu lato), *Graduate Theses and Dissertations* (2016)).

Consumable. Means material that is edible by humans.

Crackstem. The petiole can crack or split horizontally or longitudinally. Numerous cracks in several locations along the petiole are often an indication that the variety has insufficient boron nutrition. A variety's ability to utilize boron is a physiological characteristic which is genetically controlled.

Essentially all of the physiological and morphological characteristics. A plant having essentially all of the physiological and morphological characteristics of a designated plant has all of the characteristics of the plant that are otherwise present when compared in the same environment, other than an occasional variant trait that might arise during backcrossing or direct introduction of a transgene.

$F_{\#}$. The "F" symbol denotes the filial generation, and the # is the generation number, such as $F_1$, $F_2$, $F_3$, etc.

$F_1$ hybrid. The first-generation progeny of the cross of two nonisogenic plants.

Feather leaf. Feather Leaf is a yellowing of the lower leaflets and generally occurs in the outer petioles but can also be found on inner petioles of the stalk. These yellowing leaves which would normally remain in the harvested stalk are considered unacceptable. These petioles then have to be stripped off in order to meet USDA standards which effectively decreases the stalk size and yield.

Flare. The lower, generally wider portion of the petiole which is usually a paler green or white. Some also refer to this as the spoon, scoop, or shovel.

*Fusarium* yellows. A fungal soilborne disease caused by *Fusarium oxysporum* f. sp. *apii* race 2 and/or race 4. Infected plants turn yellow and are stunted. Some of the large roots may have a dark brown and a water-soaked appearance. The water-conducting tissue (xylem) in the stem, crown, and root show a characteristic orange-brown discoloration. In the later stages of infection, plants remain severely stunted and yellowed and may collapse. The disease appears most severe during warm seasons, and in heavy, wet soils. Race 4 may also produce symptoms of black heart.

Gene. As used herein, "gene" refers to a segment of nucleic acid. A gene can be introduced into a genome of a species, whether from a different species or from the same species, using transformation or various breeding techniques.

Gene silencing. The interruption or suppression of the expression of a gene at the level of transcription or translation.

Genetically modified. Describes an organism that has received genetic material from another organism, or had its genetic material modified, resulting in a change in one or more of its phenotypic characteristics. Methods used to modify, introduce or delete the genetic material may include mutation breeding, genome editing, RNA interference, backcross conversion, genetic transformation, single and multiple gene conversion, and/or direct gene transfer.

Genome editing. A type of genetic engineering in which DNA is inserted, replaced, modified, or removed from a genome using artificially engineered nucleases or other targeted changes using homologous recombination. Examples include but are not limited to use of zinc finger nucleases (ZFNs), TAL effector nucleases (TALENs), endonucleases, meganucleases, CRISPR/Cas9, and other CRISPR related technologies. (Ma et. al., *Molecular Plant,* 9:961-974 (2016); Belhaj et. al., *Current Opinion in Biotechnology,* 32:76-84 (2015)).

Gross yield (Pounds/Acre). The total yield in pounds/acre of trimmed celery plants (stalks).

Leaf celery (*Apium graveolens* L. var. *secalinum*). A plant that has been developed primarily for leaf and seed production. Often grown in Mediterranean climates, leaf celery more closely resembles celery's wild ancestors. The stems are small and fragile and vary from solid to hollow and the leaves are fairly small and are generally bitter. This type is often used for its medicinal properties and spice.

Leaf margin chlorosis. A magnesium deficiency producing an interveinal chlorosis which starts at the margin of leaves.

Maturity date. Maturity in celery can be dictated by two conditions. The first, or true maturity, is the point in time when the celery reaches maximum size distribution, but before defects such as pith, yellowing, Feather Leaf or Brown Stem appear. The second, or market maturity is an artificial maturity dictated by market conditions, i.e, the market requirement may be for 3 dozen sizes, so the field is harvested at slightly below maximum yield potential because the smaller sizes are what the customers prefer at that moment.

Muck. Muck is a soil made up primarily of humus drained from swampland. It is used for growing specialty crops, such as onions, carrots, celery, and potatoes.

MUN. MUN refers to the MUNSELL Color Chart which publishes an official color chart for plant tissues according to a defined numbering system. The chart may be purchased from the Macbeth Division of Kollmorgen Instruments Corporation, 617 Little Britain Road, New Windsor, New York 12553-6148.

Petiole. A petiole is the stem or limb of a leaf, the primary portion of the celery consumed.

Petiole depth. The average measurement in millimeters of the depth of the celery petiole at its narrowest point. The petiole depth measurement is taken from the outside of the petiole (which is the part of the petiole that faces the outside of the stalk) and is measured to the inside of the petiole or cup or the inner most point of the petiole that faces the center of the stalk or heart.

Petiole width. The average measurement of the width of the celery petiole in millimeters at its widest point. The measurement is taken from the side or edge of petiole to the opposite side or edge of the petiole. The measurement is taken 90 degrees from petiole depth.

Phthalides. One of the chemical compounds that are responsible for the characteristic flavor and aroma of celery.

Pith. Pith is a sponginess/hollowness/white discoloration that occurs in the petioles of celery varieties naturally as they become over-mature. In some varieties it occurs at an earlier stage causing harvest to occur prior to ideal maturity. Pith generally occurs in the outer, older petioles first. If it occurs, these petioles are stripped off to make grade, which effectively decreases the stalk size and overall yield potential.

Plant height. The height of the plant from the bottom of the base or butt of the celery plant to the top of the tallest leaf.

Polyphenol oxidase (PPO). An enzyme that catalyzes the conversion of phenolic compounds to quinones and assists their products' polymerization. The catalysis of PPO, in the presence of oxygen, leads to the formation of undesirable brown pigments and off-flavored products.

Quantitative Trait Loci. Quantitative Trait Loci (QTL) refers to genetic loci that control to some degree, numerically representable traits that are usually continuously distributed.

Regeneration. Regeneration refers to the development of a plant from tissue culture.

Ribbing. The texture of the exterior surface of the celery petiole can vary from smooth to ribby depending on the variety. Ribbing is the presence of numerous ridges that run vertically along the petioles of the celery plant.

Seed stem. A seed stem is the result of the elongation of the main stem of the celery, which is usually very compressed to almost non-existent, to form the flowering axis. The seed stem or flowering axis can reach several feet in height during full flower. The length of the seed stem is measured as the distance from the top of the basal plate (the base of the seed stem) to its terminus (the terminal growing point).

*Septoria apiicola*. A fungus that is the cause of late blight in celery. Symptoms include chlorotic spots that turn brown and necrotic.

Single gene converted. Single gene converted or conversion plant refers to plants which are developed by backcrossing, or via genetic engineering, wherein essentially all of the desired morphological and physiological characteristics of a line are recovered in addition to the single gene transferred into the line via the backcrossing technique or via genetic engineering.

Stalk. A stalk is a single celery plant that is trimmed with the top or foliage and the roots removed.

Standard stem celery. A more traditional stem celery with moderate joint length, to be utilized and marketed as a whole stalk with 12 to 14 inch cut or for hearts in retail environment.

Stringiness. Stringiness is a physiological characteristic that is generally associated with strings that get stuck between the consumer's teeth. There are generally two sources of strings in celery. One is the vascular bundle which can be fairly elastic and behave as a string. The second is a strip of particularly strong epidermis cells called schlerenchyma which are located on the surface of the ridges of the celery varieties that have ribs.

Suckers. Suckers are auxiliary shoots that form at the base of the stalk or within the auxiliary buds between each petiole. If these shoots form between the petioles of the stalk, several petioles have to be stripped off causing the celery to become smaller and the functional yields to be decreased.

Tall stem celery. A stem celery with especially long petioles with primary purpose of being utilized for production of sticks or limbs.

Transgene. A nucleic acid of interest that can be introduced into the genome of a plant by genetic engineering techniques (e.g., transformation) or breeding.

Celery cultivar TBG 47 is a long class celery excellently suited for use in processing in Southern California production region (Ventura County). Its characteristic long petioles, compact head, cylindrical shape, and small heart ensure very efficient use in the production of celery sticks. Its primary advantage compared to all other long class celery varieties is improved tolerance to both *Fusarium oxysporum* f. sp. *apii* Race 2 and Race 4. While other varieties have demonstrated tolerance to fusarium race 2, TBG 47 has a special advantage due to its concurrent tolerance to race 4 which is currently spreading throughout the Ventura production district while sporadically being observed in the Northern California production area (Salinas Valley) and recently reported in China.

While TBG 47 has a profound advantage in the production windows in Southern California when fusarium race 4 is problematic, in environments where there is little to no fusarium race 4 or windows when it is not prolific, its advantage is significantly diminished due to lower yields.

Celery cultivar TBG 47 has the following morphologic and other characteristics (based primarily on data collected in Oxnard, California):

TABLE 1

| VARIETY DESCRIPTION INFORMATION |
|---|
| Maturity: 94 days in Oxnard, California |
| Plant height: 94.0 cm |
| Number of outer petioles (>35.6 cm): 10.3 |
| Number of inner petioles (<35.6 cm): 4.9 |
| Stalk shape: Cylindrical |
| Stalk conformation: Compact |
| Heart formation: Low |
| Petiole length (from butt to first joint): 44.2 cm |
| Petiole length class: Long (>30 cm) |
| Petiole width (at petiole midpoint): 17.9 mm |
| Petiole thickness (at petiole midpoint): 9.4 mm |
| Petiole cross section shape: Cup |
| Petiole color (un-blanched at harvest): MUN 5GY 6/6 |
| Anthocyanin: Absent |
| Stringiness: Slight |
| Ribbing: Smooth to slight rib |
| Glossiness: Glossy |
| Leaf blade color: MUN 5GY 4/4 |
| Bolting tolerance: Susceptible |
| Stress tolerance: |
| Adaxial crackstem (boron deficiency): Tolerant |
| Abaxial crackstem (boron deficiency): Tolerant |
| Leaf margin chlorosis (magnesium deficiency): Tolerant |
| Blackheart (calcium deficiency): Tolerant |
| Pithiness (nutritional deficiency): Moderately tolerant |
| Feather leaf: Moderately tolerant |
| Sucker development: Tolerant |
| Disease resistance: |
| Brown stem (*Pseudomonas cichorii*): Tolerant |
| *Fusarium oxysporum* f. sp. *apii* race 2: Tolerant |
| *Fusarium oxysporum* f. sp. *apii* race 4: Tolerant |

This invention is also directed to methods for producing a celery plant by crossing a first parent celery plant with a second parent celery plant, wherein the first parent celery plant or second parent celery plant is celery cultivar TBG 47. Further, both the first parent celery plant and second parent celery plant may be from celery cultivar TBG 47. Still further, this invention also is directed to methods for producing a cultivar TBG 47-derived celery plant by crossing cultivar TBG 47 with a second celery plant and growing the progeny seed and repeating the crossing and growing steps with the cultivar TBG 47-derived plant from 0 to 7 times. Thus, any such methods using the cultivar TBG 47 are part of this invention: selfing, backcrosses, hybrid production, crosses to populations, and the like. All plants produced using cultivar TBG 47 as a parent are within the scope of this invention, including plants derived from cultivar TBG 47. Advantageously, cultivar TBG 47 can be used in crosses with other, different cultivars to produce first generation (F1) celery seeds and plants with superior characteristics.

Additional methods include, but are not limited to, expression vectors introduced into plant tissues using a direct gene transfer method such as microprojectile-mediated delivery, DNA injection, electroporation and the like. More preferable, expression vectors are introduced into plant tissues by using either microprojectile-mediated delivery with a biolistic device or by using *Agrobacterium*-mediated transformation. Transformant plants obtained with the protoplasm of the invention are intended to be within the scope of this invention.

As used herein, the term "plant" includes plant cells, plant protoplasts, plant cell tissue cultures from which celery plants can be regenerated, plant calli, plant clumps and plant cells that are intact in plants or parts of plants, such as leaves, pollen, embryos, meristematic cells, hypocotyls, roots, root tips, anthers, pistils, flowers, seeds, stems, and the like.

FURTHER EMBODIMENTS OF THE INVENTION

Celery in general is an important and valuable vegetable crop. Thus, a continuing goal of celery plant breeders is to develop stable, high yielding celery cultivars that are agronomically sound. To accomplish this goal, the celery breeder must select and develop celery plants with traits that result in superior cultivars.

Plant breeding techniques known in the art and used in a celery plant breeding program include, but are not limited to, pedigree breeding, recurrent selection, mass selection, single or multiple-seed descent, bulk selection, backcrossing, open pollination breeding, restriction fragment length polymorphism enhanced selection, genetic marker enhanced selection, making double haploids, and transformation. Often combinations of these techniques are used. The development of celery varieties in a plant breeding program requires, in general, the development and evaluation of homozygous varieties. There are many analytical methods available to evaluate a new variety. The oldest and most traditional method of analysis is the observation of phenotypic traits, but genotypic analysis may also be used.

Using Celery Cultivar TBG 47 to Develop Other Celery Varieties

This invention also is directed to methods for producing a celery plant by crossing a first parent celery plant with a second parent celery plant wherein the first or second parent celery plant is a celery plant of cultivar TBG 47. Further, both first and second parent celery plants can come from celery cultivar TBG 47. Also provided are methods for producing a celery plant having substantially all of the morphological and physiological characteristics of cultivar TBG 47, by crossing a first parent celery plant with a second parent celery plant wherein the first and/or the second parent celery plant is a plant having substantially all of the morphological and physiological characteristics of cultivar TBG 47 as determined at the 5% significance level when grown in the same environmental conditions. The other parent may be any celery plant, such as a celery plant that is part of a synthetic or natural population. Thus, any such methods using celery cultivar TBG 47 are part of this invention: selfing, backcrosses, hybrid production, crosses to populations, and the like. All plants produced using celery cultivar TBG 47 as at least one parent are within the scope of this invention, including those developed from cultivars derived from celery cultivar TBG 47.

The cultivar of the invention can also be used for transformation where exogenous genes are introduced and expressed by the cultivar of the invention. Genetic variants created either through traditional breeding methods using celery cultivar TBG 47 or through transformation of cultivar TBG 47 by any of a number of protocols known to those of skill in the art are intended to be within the scope of this invention.

The following describes breeding methods that may be used with celery cultivar TBG 47 in the development of further celery plants. One such embodiment is a method for developing a progeny celery plant in a celery plant breeding program comprising: obtaining the celery plant, or a part thereof, of cultivar TBG 47, utilizing said plant or plant part as a source of breeding material, and selecting a celery cultivar TBG 47 progeny plant with molecular markers in common with cultivar TBG 47 and/or with morphological and/or physiological characteristics of celery cultivar TBG 47. Breeding steps that may be used in the celery plant breeding program include, but are not limited to, pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of celery cultivar TBG 47 progeny celery plants, comprising crossing cultivar TBG 47 with another celery plant, thereby producing a population of celery plants, which, on average, derive 50% of their alleles from celery cultivar TBG 47. A plant of this population may be selected and repeatedly selfed or sibbed with a celery cultivar resulting from these successive filial generations. One embodiment of this invention is the celery cultivar produced by this method and that has obtained at least 50% of its alleles from celery cultivar TBG 47.

Still yet another aspect of the invention is a method of producing a celery plant derived from the celery cultivar TBG 47, the method comprising the steps of: (a) preparing a progeny plant derived from celery cultivar TBG 47 by crossing a plant of the celery cultivar TBG 47 with a second celery plant; and (b) crossing the progeny plant with itself or a second plant to produce a seed of a progeny plant of a subsequent generation which is derived from a plant of the celery cultivar TBG 47. In further embodiments of the invention, the method may additionally comprise: (c) growing a progeny plant of a subsequent generation from said seed of a progeny plant of a subsequent generation and crossing the progeny plant of a subsequent generation with itself or a second plant; and repeating the steps for an additional 2-10 generations to produce a celery plant derived from the celery cultivar TBG 47. The plant derived from celery cultivar TBG 47 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from celery cultivar TBG 47 is obtained which possesses some of the desirable traits of the line as well as potentially other selected traits. Also provided by the invention is a plant produced by this and the other methods of the invention.

In another embodiment of the invention, the method of producing a celery plant derived from the celery cultivar TBG 47 further comprises: (a) crossing the celery cultivar TBG 47-derived celery plant with itself or another celery plant to yield additional celery cultivar TBG 47-derived progeny celery seed; (b) growing the progeny celery seed of step (a) under plant growth conditions to yield additional celery cultivar TBG 47-derived celery plants; and (c) repeating the crossing and growing steps of (a) and (b) to generate further celery cultivar TBG 47-derived celery plants. In specific embodiments, steps (a) and (b) may be repeated at least 1, 2, 3, 4, or 5 or more times as desired. The invention further provides a celery plant produced by this and the foregoing methods.

Progeny of celery cultivar TBG 47 may also be characterized through their filial relationship with celery cultivar TBG 47, as for example, being within a certain number of breeding crosses of celery cultivar TBG 47. A breeding cross is a cross made to introduce new genetics into the progeny, and is distinguished from a cross, such as a self or a sib cross, made to select among existing genetic alleles. The lower the number of breeding crosses in the pedigree, the closer the relationship between celery cultivar TBG 47 and its progeny. For example, progeny produced by the methods described herein may be within 1, 2, 3, 4 or 5 breeding crosses of celery cultivar TBG 47.

One of ordinary skill in the art of plant breeding would know how to evaluate the traits of two plant varieties to determine if there is no significant difference between the two traits expressed by those varieties. For example, see Fehr and Walt, *Principles of Cultivar Development*, pp. 261-286 (1987). Thus the invention includes celery cultivar TBG 47 progeny celery plants comprising a combination of at least two cultivar TBG 47 traits selected from the group consisting of those listed in Table 1 or the cultivar TBG 47 combination of traits listed in the Detailed Description of the Invention, so that said progeny celery plant is not significantly different for said traits than celery cultivar TBG 47 as determined at the 5% significance level when grown in the same environmental conditions. Using techniques described herein, molecular markers may be used to identify said progeny plant as a celery cultivar TBG 47 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

The goal of celery plant breeding is to develop new, unique, and superior celery cultivars. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level and the cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. Therefore, two breeders will never develop the same line, or even very similar lines, having the same celery traits.

Pedigree breeding is used commonly for the improvement of self-pollinating crops or inbred lines of cross-pollinating crops. Pedigree breeding starts with the crossing of two genotypes, such as celery cultivar TBG 47 or a celery variety having all of the morphological and physiological characteristics of TBG 47, and another celery variety having one or more desirable characteristics that is lacking or which complements celery cultivar TBG 47. If the two original parents do not provide all the desired characteristics, other sources can be included in the breeding population. In the pedigree method, superior plants are selfed and selected in successive filial generations. In the succeeding filial generations, the heterozygous condition gives way to the homozygous allele condition as a result of inbreeding. Typically, in the pedigree method of breeding, five or more successive filial generations of selfing and selection is practiced: $F_1$ to $F_2$; $F_2$ to $F_3$; $F_3$ to $F_4$; $F_4$ to $F_5$; etc. In some examples, 1, 2, 3, 4, 5, 6, 7, 8, 9, 10, or more generations of selfing and selection are practiced. After a sufficient amount of inbreeding, successive filial generations will serve to increase seed of the developed variety. Preferably, the developed variety comprises homozygous alleles at about 95% or more of its loci.

In addition to being used to create backcross conversion populations, backcrossing can also be used in combination with pedigree breeding. As discussed previously, backcrossing can be used to transfer one or more specifically desirable traits from one variety (the donor parent) to a developed variety (the recurrent parent), which has good overall agronomic characteristics yet may lack one or more other desirable traits. However, the same procedure can be used to move the progeny toward the genotype of the recurrent parent but at the same time retain many components of the non-recurrent parent by stopping the backcrossing at an early stage and proceeding with selfing and selection. For example, a celery variety may be crossed with another variety to produce a first-generation progeny plant. The first-generation progeny plant may then be backcrossed to one of its parent varieties to create a $F_1BC_1$. Progeny are selfed and selected so that the newly developed variety has many of the attributes of the recurrent parent and yet several of the desired attributes of the donor parent. This approach leverages the value and strengths of both parents for use in new celery varieties.

Therefore, in some examples a method of making a backcross conversion of celery cultivar TBG 47, comprising the steps of crossing a plant of celery cultivar TBG 47 or a celery variety having all of the morphological and physiological characteristics of TBG 47 with a donor plant possessing a desired trait to introduce the desired trait, selecting an $F_1$ progeny plant containing the desired trait, and backcrossing the selected $F_1$ progeny plant to a plant of celery cultivar TBG 47 are provided. This method may further comprise the step of obtaining a molecular marker profile of celery cultivar TBG 47 and using the molecular marker profile to select for a progeny plant with the desired trait and the molecular marker profile of TBG 47. The molecular marker profile can comprise information from one or more markers. In one example the desired trait is a mutant gene or transgene present in the donor parent. In another example, the desired trait is a native trait in the donor parent.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

The single-seed descent procedure in the strict sense refers to planting a segregating population, harvesting a sample of one seed per plant, and using the one-seed sample to plant the next generation. When the population has advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Mutation breeding is another method of introducing new traits into celery varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in "Principles of Cultivar Development" by Fehr, Macmillan Publishing Company, 1993. In addition, mutations created in other celery plants may be used to produce a backcross conversion of celery cultivar TBG 47 that comprises such mutation.

Selection of celery plants for breeding is not necessarily dependent on the phenotype of a plant and instead can be based on genetic investigations. For example, one may utilize a suitable genetic marker which is closely associated with a trait of interest. One of these markers may therefore be used to identify the presence or absence of a trait in the offspring of a particular cross, and hence may be used in selection of progeny for continued breeding. This technique may commonly be referred to as marker-assisted selection. Any other type of genetic marker or other assay which is able to identify the relative presence or absence of a trait of interest in a plant may also be useful for breeding purposes. Procedures for marker assisted selection applicable to the breeding of celeries are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Isozyme Electrophoresis, Restriction Fragment Length Polymorphisms (RFLPs), Simple Sequence Length Polymorphisms (SSLPs) (Williams et al., Nucleic Acids Res., 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), Simple Sequence Repeats (SSRs), and Single Nucleotide Polymorphisms (SNPs) (Wang et al., Science, 280:1077-1082, 1998).

The production of double haploids can also be used for the development of homozygous varieties in a breeding program. Double haploids are produced by the doubling of a set of chromosomes from a heterozygous plant to produce a completely homozygous individual. For example, see, Wan, et al., "Efficient Production of Doubled Haploid Plants Through Colchicine Treatment of Anther-Derived Maize Callus," *Theoretical and Applied Genetics,* 77:889-892 (1989) and U.S. Pat. No. 7,135,615. This can be advantageous because the process omits the generations of selfing needed to obtain a homozygous plant from a heterozygous source.

Descriptions of other breeding methods that are commonly used for different traits and crops can be found in one of several reference books (e.g., Allard, "Principles of plant breeding," John Wiley & Sons, NY, University of California, Davis, Calif, 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: Soybeans: Improvement, Production and Uses," 2d Ed., Manograph 16:249, 1987; Fehr, "Principles of cultivar development," Theory and Technique (Vol 1) and Crop Species Soybean (Vol 2), Iowa State Univ., Macmillian Pub. Co., NY, 360-376, 1987; Poehlman and Sleper, "Breeding Field Crops" Iowa State University Press, Ames, 1995; Sprague and Dudley, eds., Corn and Improvement, 5th ed., 2006).

Genotypic Profile of TBG 47 and Progeny

In addition to phenotypic observations, a plant can also be identified by its genotype. The genotype of a plant can be characterized through a genetic marker profile which can identify plants of the same variety or a related variety, or which can be used to determine or validate a pedigree. Genetic marker profiles can be obtained by techniques such as restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs) also referred to as microsatellites, single nucleotide polymorphisms (SNPs), or genome-wide evaluations such as genotyping-by-sequencing (GBS). For example, see Cregan et al. (1999) "An Integrated Genetic Linkage Map of the Soybean Genome" Crop Science 39:1464-1490, and Berry et al. (2003) "Assessing Probability of Ancestry Using Simple Sequence Repeat Profiles: Applications to Maize Inbred Lines and Soybean Varieties" Genetics 165:331-342, each of which are incorporated by reference herein in their entirety. Favorable genotypes and or marker profiles, optionally associated with a trait of interest, may be identified by one or more methodologies.

In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) *Nat Biotech* 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) *Nat Rev Genet* 11:31-46; and, Egan et al. (2012) *Am J Bot* 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) *PLoS ONE* 6:e19379), and expression methods. In some examples, no reference genome sequence is needed in order to complete the analysis.

With any of the genotyping techniques mentioned herein, polymorphisms may be detected when the genotype and/or sequence of the plant of interest is compared to the genotype and/or sequence of one or more reference plants. The polymorphism revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers. The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

The invention further provides a method of determining the genotype of a plant of celery cultivar TBG 47, or a first-generation progeny thereof, comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The plurality of polymorphisms are indicative of and/or give rise to the expression of the morphological and physiological characteristics of celery cultivar TBG 47. The invention further provides a computer readable medium produced by such a method.

In some examples, a plant, a plant part, or a seed of celery cultivar TBG 47 may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, and the like. A molecular profile may also be a nucleic acid sequence profile, and/or a physical map. A phenotypic profile may include, but is not limited to, a protein expression profile, a metabolic profile, an mRNA expression profile, and the like.

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.,* 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Particular markers used for these purposes are not limited to the set of markers disclosed herein but may include any type of marker and marker profile which provides a means of distinguishing varieties. In addition to being used for identification of celery cultivar TBG 47, a hybrid produced through the use of TBG 47, and the identification or verification of pedigree for progeny plants produced through the use of TBG 47, a genetic marker profile is also useful in developing a gene conversion of TBG 47.

Means of performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present.

The SSR profile of celery cultivar TBG 47 can be used to identify plants comprising celery cultivar TBG 47 as a parent, since such plants will comprise the same homozygous alleles as celery cultivar TBG 47. Because the celery variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of celery cultivar TBG 47 in their development, such as celery cultivar TBG 47 comprising a gene conversion, backcross conversion, transgene, or genetic sterility factor, may be identified by having a molecular marker profile with a high percent identity to celery cultivar TBG 47. Such a percent identity might be 95%, 96%, 97%, 98%, 99%, 99.5%, or 99.9% identical to celery cultivar TBG 47.

The SSR profile of celery cultivar TBG 47 can also be used to identify essentially derived varieties and other progeny varieties developed from the use of celery cultivar TBG 47, as well as cells and other plant parts thereof. Such plants may be developed using the markers identified in WO 00/31964, U.S. Pat. Nos. 6,162,967, and 7,288,386. Progeny plants and plant parts produced using celery cultivar TBG 47 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from celery cultivar TBG 47, as measured by either percent identity or percent similarity. Such progeny may be further characterized as being within a pedigree distance of celery cultivar TBG 47, such as within 1, 2, 3, 4, or 5 or less cross-pollinations to a celery plant other than celery cultivar TBG 47 or a plant that has celery cultivar TBG 47 as a progenitor. Unique molecular profiles may be identified with other molecular tools such as SNPs and RFLPs.

While determining the genotypic profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Molecular data from TBG 47 may be used in a plant breeding process. Nucleic acids may be isolated from a seed of TBG 47 or from a plant, plant part, or cell produced by growing a seed of TBG 47, or from a seed of TBG 47 with a gene conversion, or from a plant, plant part, or cell of TBG 47 with a gene conversion. One or more polymorphisms may be isolated from the nucleic acids. A plant having one or more of the identified polymorphisms may be selected and used in a plant breeding method to produce another plant.

In another embodiment of the invention, the genetic complement of the celery cultivar TBG 47 is provided. The phrase "genetic complement" is used to refer to the aggregate of nucleotide sequences, the expression of which sequences defines the phenotype of, in the present case, a celery plant, or a cell or tissue of that plant. A genetic complement thus represents the genetic makeup of a cell, tissue or plant, and a hybrid genetic complement represents the genetic makeup of a hybrid cell, tissue or plant. The invention thus provides celery plant cells that have a genetic complement in accordance with the celery plant cells disclosed herein, and plants, seeds and plants containing such cells. Plant genetic complements may be assessed by genetic marker profiles, and by the expression of phenotypic traits that are characteristic of the expression of the genetic complement, e.g., isozyme typing profiles.

Introduction of a New Trait or Locus into Celery Cultivar TBG 47

Cultivar TBG 47 represents a new base genetic variety into which a new gene, locus or trait may be introgressed. Backcrossing and direct transformation represent two important methods that can be used to accomplish such an introgression.

Single Gene (Locus) Conversions

When the term "celery plant" is used in the context of the present invention, this also includes any single gene or locus conversions of that variety. The term "single locus converted plant" or "single gene converted plant" refers to those celery plants which are developed by backcrossing or genetic engineering, wherein essentially all of the desired morphological and physiological characteristics of a variety are recovered in addition to the one or more genes transferred into the variety via the backcrossing technique or genetic engineering. Backcrossing methods can be used with the present invention to improve or introduce a characteristic into the variety.

A backcross conversion of celery cultivar TBG 47 occurs when DNA sequences are introduced through backcrossing (Hallauer, et al., "Corn Breeding," *Corn and Corn Improvements*, No. 18, pp. 463-481 (1988)), with celery cultivar TBG 47 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, *Proceedings Symposium of the Analysis of Molecular Data*, Crop Science Society of America, Corvallis, Oregon (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. (See, Hallauer, et al., *Corn and Corn Improvement*, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, modified fatty acid metabolism, modified carbohydrate metabolism, industrial enhancements, yield stability, yield enhancement, disease resistance (bacterial, fungal, or viral), insect resistance, and herbicide resistance. In addition, an introgression site itself, such as an FRT site, Lox site, or other site-specific integration site, may be inserted by backcrossing and utilized for direct insertion of one or more genes of interest into a specific plant variety.

A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site-specific integration system allows for the integration of multiple genes at a known recombination site in the genome. At least one, at least two or at least three and less than ten, less than nine, less than eight, less than seven, less than six, less than five or less than four locus conversions may be introduced into the plant by backcrossing, introgression or transformation to express the desired trait, while the plant, or a plant grown from the seed, plant part or plant cell, otherwise retains the phenotypic characteristics of the deposited seed when grown under the same environmental conditions.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in celery cultivar TBG 47 comprises crossing celery cultivar TBG 47 plants grown from celery cultivar TBG 47 seed with plants of another celery variety that comprise the desired trait, gene or locus, selecting $F_1$ progeny plants that comprise the desired trait, gene or locus to produce selected $F_1$ progeny plants, crossing the selected progeny plants with the celery cultivar TBG 47 plants to produce backcross progeny plants, selecting for backcross progeny plants that have the desired trait, gene or locus and the morphological characteristics of celery cultivar TBG 47 to produce selected backcross progeny plants, and backcrossing to celery cultivar TBG 47 three or more times in succession to produce selected fourth or higher backcross progeny plants that comprise said trait, gene or locus. The modified celery cultivar TBG 47 may be further characterized as having the physiological and morphological characteristics of celery cultivar TBG 47 as determined at the 5% significance level when grown in the same environmental conditions and/or may be characterized by percent similarity or identity to celery cultivar TBG 47 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny celery seed by adding a step at the end of the process that comprises crossing celery cultivar TBG 47 with the introgressed trait or locus with a different celery plant and harvesting the resultant first generation progeny celery seed.

Methods for Genetic Engineering of Celery

With the advent of molecular biological techniques that have allowed the isolation and characterization of genes that encode specific protein products, scientists in the field of plant biology developed a strong interest in engineering the genome of plants (genetic engineering) to contain and express foreign genes, or additional, or modified versions of native, or endogenous genes (perhaps driven by different promoters) in order to alter the traits of a plant in a specific manner. Plants altered by genetic engineering are often referred to as 'genetically modified'. Any DNA sequences, whether from a different species or from the same species, which are introduced into the genome using transformation and/or various breeding methods, are referred to herein collectively as "transgenes." Over the last fifteen to twenty years several methods for producing transgenic plants have been developed, and the present invention, in particular embodiments, also relates to transformed versions of the claimed cultivar.

Vectors used for the transformation of celery cells are not limited so long as the vector can express an inserted DNA in the cells. For example, vectors comprising promoters for constitutive gene expression in celery cells (e.g., cauliflower mosaic virus 35S promoter) and promoters inducible by exogenous stimuli can be used. Examples of suitable vectors include pBI binary vector. The "celery cell" into which the vector is to be introduced includes various forms of celery cells, such as cultured cell suspensions, protoplasts, leaf sections, and callus. A vector can be introduced into celery cells by known methods, such as the polyethylene glycol method, polycation method, electroporation, *Agrobacterium*-mediated transfer, particle bombardment and direct DNA uptake by protoplasts. See, e.g., Pang et al. (The Plant J., 9, 899-909, 1996).

Numerous methods for plant transformation have been developed, including biological and physical, plant transformation protocols. See, for example, Miki, et al., "Procedures for Introducing Foreign DNA into Plants" in Methods in Plant Molecular Biology and Biotechnology, Glick and Thompson (Eds.), CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson (Eds.), CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.*, 8:238 (1989). See also, U.S. Pat. No. 5,563,055 (Townsend and Thomas), issued Oct. 8, 1996.

*Agrobacterium*-mediated transfer is a widely applicable system for introducing gene loci into plant cells, including celery. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., Bio. Tech., 3(7): 637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio. Tech.*, 3(7):629-635, 1985; U.S. Pat. No. 5,563,055). For example, U.S. Pat. No. 5,349,124 describes a method of transforming celery plant cells using *Agrobacterium*-mediated transformation. By inserting a chimeric gene having a DNA coding sequence encoding for the full-length B.t. toxin protein that expresses a protein toxic toward Lepidopteran larvae, this methodology resulted in celery having resistance to such insects.

B. Direct Gene Transfer:

Several methods of plant transformation, collectively referred to as direct gene transfer, have been developed as an alternative to *Agrobacterium*-mediated transformation. A generally applicable method for delivering transforming DNA segments to plant cells is microprojectile-mediated transformation, or microprojectile bombardment. In this method, particles are coated with nucleic acids and delivered into cells by a propelling force. Sanford, et al., *Part. Sci. Technol.*, 5:27 (1987); Sanford, J. C., *Trends Biotech.*, 6:299 (1988); Klein, et al., *Bio/technology*, 6:559-563 (1988); Sanford, J. C., *Physiol Plant*, 7:206 (1990); Klein, et al., *Bio/technology*, 10:268 (1992). See also, U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang, et al., *Bio/technology*, 9:996 (1991). Alternatively, liposome and spheroplast fusion have been used to introduce expression vectors into plants. Deshayes, et al., *EMBO J.*, 4:2731 (1985); Christou, et al., *PNAS*, 84:3962 (1987). Direct uptake of DNA into protoplasts using $CaCl_2$) precipitation, calcium phosphate precipitation, polyethylene glycol treatment, polyvinyl alcohol, or poly-L-ornithine has also been reported. See, e.g., Potrykus et al., *Mol. Gen. Genet.,* 199:183-188, 1985; Omirulleh et al., *Plant Mol. Biol.,* 21(3):415-428, 1993; Fromm et al., *Nature,* 312:791-793, 1986; Uchimiya et al., *Mol. Gen. Genet.,* 204:204, 1986; Marcotte et al., *Nature,* 335: 454, 1988; Hain, et al., *Mol. Gen. Genet.,* 199:161, 1985 and Draper, et al., *Plant Cell Physiol.* 23:451, 1982.

Electroporation of protoplasts and whole cells and tissues has also been described. Donn, et al., In Abstracts of VIIth International Congress on Plant Cell and Tissue Culture IAPTC, A2-38, p. 53, 1990; D'Halluin, et al., *Plant Cell,* 4:1495-1505, 1992; and Spencer, et al., *Plant Mol. Biol.,* 24:51-61, 1994. Another illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target celery cells.

Transformation of plants and expression of foreign genetic elements is exemplified in Choi et al., *Plant Cell Rep.,* 13: 344-348, 1994 and Ellul et al., *Theor. Appl. Genet.,* 107:462-469, 2003.

Following transformation of celery target tissues, expression of selectable marker genes allows for preferential selection of transformed cells, tissues, and/or plants, using regeneration and selection methods now well known in the art.

The methods described herein for transformation would typically be used for producing a transgenic variety. The transgenic variety could then be crossed, with another (non-transformed or transformed) variety, in order to produce a new transgenic variety. Alternatively, a genetic trait which has been engineered into a particular celery cultivar using the transformation techniques described could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Expression Vectors for Celery Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals which confers resistance to kanamycin. Fraley et al., *Proc. Natl. Acad. Sci. U.S.A.,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.,* 210:86 (1987), Svab et al., *Plant Mol. Biol.* 14:197 (1990) Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988). Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic CellMol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS, α-galactosidase, luciferase and chloramphenicol, acetyltransferase. Jefferson, R. A., *Plant Mol. Biol.* Rep. 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for Celery Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in celery. Optionally, the inducible promoter is operably linked to a nucleotide sequence encoding a signal sequence which is operably linked to a gene for expression in celery. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters:

A constitutive promoter is operably linked to a gene for expression in celery or the constitutive promoter is operably linked to a nucleotide sequence encoding a signal sequence which is operably linked to a gene for expression in celery.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT application WO 96/30530.

C. Tissue-Specific or Tissue-Preferred Promoters:

A tissue-specific promoter is operably linked to a gene for expression in celery. Optionally, the tissue-specific promoter is operably linked to a nucleotide sequence encoding a signal sequence which is operably linked to a gene for expression in celery. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499-509 (1984), Steifel, et al., Expression of a maize cell wall hydroxyproline-rich glycoprotein gene in early leaf and root vascular differentiation, *Plant Cell* 2:785-793 (1990).

Additional Methods for Genetic Engineering of Celery

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see e.g., WO 2009/114321; Gao et al. (2010) *Plant Journal* 1:176-187). Another site-directed engineering method is through the use of zinc finger domain recognition coupled with the restriction properties of restriction enzyme. See e.g., Urnov, et al., (2010) *Nat Rev Genet.* 11(9):636-46; Shukla, et al., (2009) *Nature* 459 (7245):437-41. A transcription activator-like (TAL) effector-DNA modifying enzyme (TALE or TALEN) is also used to engineer changes in plant genome. See e.g., US20110145940, Cermak et al., (2011) *Nucleic Acids Res.* 39(12) and Boch et al., (2009), *Science* 326(5959): 1509-12. Site-specific modification of plant genomes can also be performed using the bacterial type II CRISPR (clustered regularly interspaced short palindromic repeats)/Cas (CRISPR-associated) system, as well as similar CRISPR related technologies. See e.g., Belhaj et al., (2013), *Plant Methods* 9: 39; The Cas9/guide RNA-based system allows targeted cleavage of genomic DNA guided by a customizable small noncoding RNA in plants (see e.g., WO 2015026883A1, incorporated herein by reference).

A genetic map can be generated that identifies the approximate chromosomal location of an integrated DNA molecule, for example via conventional restriction fragment length polymorphisms (RFLP), polymerase chain reaction (PCR) analysis, simple sequence repeats (SSR), and single nucleotide polymorphisms (SNP). For exemplary methodologies in this regard, see Glick and Thompson, *Methods in Plant Molecular Biology and Biotechnology*, pp. 269-284 (CRC Press, Boca Raton, 1993).

Wang et al. discuss "Large Scale Identification, Mapping and Genotyping of Single-Nucleotide Polymorphisms in the Human Genome", *Science* (1998) 280:1077-1082, and similar capabilities are increasingly available for the celery genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons could involve hybridizations, RFLP, PCR, SSR, sequencing or combinations thereof, all of which are conventional techniques. SNPs may also be used alone or in combination with other techniques.

Celery Cultivar TBG 47 Further Comprising a Transgene

Transgenes and transformation methods provide means to engineer the genome of plants to contain and express heterologous genetic elements, including but not limited to foreign genetic elements, additional copies of endogenous elements, and/or modified versions of native or endogenous genetic elements, in order to alter at least one trait of a plant in a specific manner. Any heterologous DNA sequence(s), whether from a different species or from the same species, which are inserted into the genome using transformation, backcrossing, or other methods known to one of skill in the art are referred to herein collectively as transgenes. The sequences are heterologous based on sequence source, location of integration, operably linked elements, or any combination thereof. One or more transgenes of interest can be introduced into celery cultivar TBG 47. Transgenic variants of celery cultivar TBG 47 plants, seeds, cells, and parts thereof or derived therefrom are provided. Transgenic variants of TBG 47 comprise the physiological and morphological characteristics of celery cultivar TBG 47, such as determined at the 5% significance level when grown in the same environmental conditions, and/or may be characterized or identified by percent similarity or identity to TBG 47 as determined by SSR or other molecular markers. In some examples, transgenic variants of celery cultivar TBG 47 are produced by introducing at least one transgene of interest into celery cultivar TBG 47 by transforming TBG 47 with a polynucleotide comprising the transgene of interest. In other examples, transgenic variants of celery cultivar TBG 47 are produced by introducing at least one transgene by introgressing the transgene into celery cultivar TBG 47 by crossing.

In one example, a process for modifying celery cultivar TBG 47 with the addition of a desired trait, said process comprising transforming a celery plant of cultivar TBG 47 with a transgene that confers a desired trait is provided. Therefore, transgenic TBG 47 celery cells, plants, plant parts, and seeds produced from this process are provided. In some examples one more desired traits may include traits such as sterility (nuclear and cytoplasmic), fertility restoration, nutritional enhancements, drought tolerance, nitrogen utilization, altered fatty acid profile, modified fatty acid metabolism, modified carbohydrate metabolism, industrial enhancements, yield stability, yield enhancement, disease resistance (bacterial, fungal, or viral), insect resistance, and herbicide resistance. The specific gene may be any known in the art or listed herein, including but not limited to a polynucleotide conferring resistance to an ALS-inhibitor herbicide, imidazolinone, sulfonylurea, protoporphyrinogen oxidase (PPO) inhibitors, hydroxyphenyl pyruvate dioxygenase (HPPD) inhibitors, glyphosate, glufosinate, triazine, 2,4-dichlorophenoxyacetic acid (2,4-D), dicamba, broxynil, metribuzin, or benzonitrile herbicides; a polynucleotide encoding a *Bacillus thuringiensis* polypeptide, a polynucleotide encoding a phytase, a fatty acid desaturase (e.g., FAD-2, FAD-3), galactinol synthase, a raffinose synthetic enzyme; or a polynucleotide conferring resistance to tipburn, *Fusarium oxysporum, Nasonovia ribisnigri, Sclerotinia sclerotiorum* or other plant pathogens.

Foreign Protein Genes and Agronomic Genes

By means of the present invention, plants can be genetically engineered to express various phenotypes of agronomic interest. Through the transformation of celery, the expression of genes can be altered to enhance disease resistance, insect resistance, herbicide resistance, agronomic, nutritional quality, and other traits. Transformation can also be used to insert DNA sequences which control or help control male-sterility. DNA sequences native to celery, as well as non-native DNA sequences, can be transformed into celery and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy, et al., *PNAS USA,* 85:8805-8809 (1988); and U.S. Pat. Nos. 5,107,065, 5,453,566, and 5,759,829); co-suppression (e.g., Taylor, *Plant Cell,* 9:1245 (1997); Jorgensen, *Trends Biotech.,* 8(12):340-344 (1990); Flavell, *PNAS USA,* 91:3490-3496 (1994); Finnegan, et al., *Bio/Technology,* 12:883-888 (1994); Neuhuber, et al., *Mol. Gen. Genet.,* 244:230-241 (1994)); RNA interference (Napoli, et al., *Plant Cell,* 2:279-289 (1990); U.S. Pat. No. 5,034,323; Sharp, *Genes Dev.,* 13:139-141 (1999); Zamore, et al., *Cell,* 101:25-33 (2000); Montgomery, et al., *PNAS USA,* 95:15502-15507 (1998)), virus-induced gene silencing (Burton, et al., *Plant Cell,* 12:691-705 (2000); Baulcombe, *Curr. Op. Plant Bio.,* 2:109-113 (1999)); target-RNA-specific ribozymes (Haseloff, et al., *Nature,* 334: 585-591 (1988)); hairpin structures (Smith, et al., *Nature,* 407:319-320 (2000); WO 99/53050; WO 98/53083); MicroRNA (Aukerman & Sakai, *Plant Cell,* 15:2730-2741 (2003)); ribozymes (Steinecke, et al., *EMBO J.,* 11:1525 (1992); Perriman, et al., *Antisense Res. Dev.,* 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary nucleotide sequences and/or native loci that confer at least one trait of interest, which optionally may be conferred or altered by genetic engineering, transformation or introgression of a transformed event include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding 6-endotoxin genes can be purchased from American Type Culture Collection, Manassas, Virginia, for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum.*

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a celery endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

S. A lettuce mosaic potyvirus (LMV) coat protein gene introduced into celery in order to increase its resistance to LMV infection. See Dinant et al., *Molecular Breeding.* 1997, 3: 1, 75-86.

T. Genes involved in the Systemic Acquired Resistance (SAR) Response and/or the pathogenesis-related genes. Briggs, S., *Current Biology,* 5(2) (1995).

U. Antifungal genes. See Cornelissen and Melchers, *Plant Physiol.,* 101:709-712 (1993); Parijs et al., *Planta* 183:258-264 (1991) and Bushnell et al., *Can. J. of Plant Path.* 20(2):137-149 (1998).

V. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif (1995).

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvlshikimate-3-phosphate synthase (EPSPS) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPs which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in *Transgenic Research.* 1999, 8: 1, 33-44 that discloses *Lactuca sativa* resistant to glufosinate. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (PPO; protox) is the target of the PPO-inhibitor class of herbicides; a PPO-inhibitor resistant PPO gene was recently identified in *Amaranthus tuberculatus* (Patzoldt et al., PNAS, 103(33):12329-2334, 2006). PPO is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

F. Genes that confer resistance to auxin or synthetic auxin herbicides. For example an aryloxyalkanoate dioxygenase (AAD) gene may confer resistance to arlyoxyalkanoate herbicides, such as 2,4-D, as well as pyridyloxyacetate herbicides, such as described in U.S. Pat. No. 8,283,522, and US2013/0035233. In other examples, a dicamba monooxygenase (DMO) is used to confer resistance to dicamba. Other polynucleotides of interest related to auxin herbicides and/or uses thereof include, for example, the descriptions found in U.S. Pat. Nos. 8,119,380; 7,812,224; 7,884,262; 7,855,326; 7,939,721; 7,105,724; 7,022,896; 8,207,092; US2011/067134; and US2010/0279866. Any of the above listed herbicide genes (1-6) can be introduced into the claimed celery cultivar through a variety of means including, but not limited to, transformation and crossing.

3. Genes that Confer or Contribute to a Value-Added Trait, Such as:

A. Increased iron content of the celery, for example by transforming a plant with a soybean ferritin gene as described in Goto et al., *Acta Horticulturae.* 2000, 521, 101-109.

B. Decreased nitrate content of leaves, for example by transforming a celery with a gene coding for a nitrate reductase. See for example Curtis et al., *Plant Cell Report.* 1999, 18:11, 889-896.

C. Increased sweetness of the celery by transferring a gene coding for monellin that elicits a flavor 100,000 times sweeter than sugar on a molar basis. See Penarrubia et al., *Biotechnology.* 1992, 10:5, 561-564.

D. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

E. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

F. Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

G. Modified bolting tolerance in plants for example, by transferring a gene encoding for gibberellin 2-oxidase (U.S. Pat. No. 7,262,340). Bolting has also been modified using non-transformation methods; see Wittwer, S. H., et al. (1957) *Science.* 126(3262): 30-31; Booij, R. et al., (1995) *Scientia Horticulturae.* 63:143-154; and Booij, R. et al., (1994) *Scientia Horticulturae.* 58:271-282.

H. Decreased browning of the celery, for example by transforming a plant with an siRNA, RNAi or microRNA vector, or other suppression sequence coding for polyphenol oxidase (PPO) to silence the expression of PPO genes. See Araji et al. (2014) *Plant Physiology* 164:1191-1203, Chi et al. (2014) *BMC Plant Biology* 14:62, and Carter, N., (2012) Petition for Determination of Nonregulated Status: Arctic™ Apple (*Malus* x *domestica*) Events GD743 and GS784, received by APHIS.

4. Genes that Control Male-Sterility

A. Introduction of a deacetylase gene under the control of a tapetum-specific promoter and with the application of the chemical N—Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

For additional examples of nuclear male and female sterility systems and genes, see also, U.S. Pat. Nos. 5,859, 341, 6,297,426, 5,478,369, 5,824,524, 5,850,014, and 6,265,640, all of which are hereby incorporated by reference.

5. Genes that Affect Abiotic Stress Resistance

Genes that affect abiotic stress resistance (including but not limited to flowering, seed development, enhancement of nitrogen utilization efficiency, altered nitrogen responsiveness, drought resistance or tolerance, cold resistance or tolerance, high or low light intensity, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723 and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), 6,713,663 (FT), 6,794,560, 6,307,126 (GAI), WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), WO 2004/076638, and WO 004/031349 (transcription factors).

Tissue Culture

Further reproduction of the variety can occur by tissue culture and regeneration. Tissue culture of various tissues of celery and regeneration of plants there from is well known and widely published. For example, reference may be had to Teng et al., *HortScience.* 1992, 27: 9, 1030-1032 Teng et al., *HortScience.* 1993, 28: 6, 669-1671, Zhang et al., *Journal of Genetics and Breeding.* 1992, 46: 3, 287-290, Webb et al., *Plant Cell Tissue and Organ Culture.* 1994, 38: 1, 77-79, Curtis et al., *Journal of Experimental Botany.* 1994, 45: 279, 1441-1449, Nagata et al., *Journal for the American Society for Horticultural Science.* 2000, 125: 6, 669-672, and Ibrahim et al., Plant Cell, Tissue and Organ Culture. (1992), 28(2): 139-145. It is clear from the literature that the state of the art is such that these methods of obtaining plants are routinely used and have a very high rate of success. Thus, another aspect of this invention is to provide cells which upon growth and differentiation produce celery plants having the physiological and morphological characteristics of variety TBG 47.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, hypocotyls, pollen, flowers, seeds, leaves, stems, roots, root tips, pistils, anthers, meristematic cells and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Industrial Uses of Celery Cultivar TBG 47

Celery may be used in a variety of manners including but not limited to, use in salads, soups, being filled with cheese, soybean, vegetable, peanut butter, or dairy type products, served raw, cooked, baked or frozen, served as sticks, pieces, diced, or dipped like potato chips, or used as straws.

Tables

In the tables that follow, the traits and characteristics of celery cultivar TBG 47 are given compared to other celery cultivars. Color references made in the Tables refer to the Munsell Color Chart. NA=not available.

Celery cultivar TBG 47 is the result of nine generations of single seed selection under production conditions where *Fusarium oxysporum* f. sp. *apii* Race 2 and/or Race 4 were prevalent and active. The $F_0$ generation was Gene's Gem 12. At each generation, seedlings having *Fusarium* resistance and long sticks were selected. The result of the selection is a long stick celery variety with improved tolerance to both fusarium race 2 (tables 2-5) and the first long stick variety with significant tolerance to race 4 (tables 5-8).

While TBG 47 has improved tolerance to *Fusarium oxysporum* f. sp. *apii* Race 2 & 4 it only has very slight tolerance to bolting compared to very susceptible varieties like TBG 27 and Stix (table 8). However, when cold temperatures are more prevalent and bolting initiation and development are generally increased for most varieties TBG 47 becomes mostly unmarketable like most susceptible varieties ADS-17, TBG 27, 52, and Stix (table 9).

Under conditions when there are few to no stressors, fusarium or bolting (tables 10-13), TBG 47 generally does not perform as well as most other varieties as noted by yield of four inch sticks (weight and count) and length of outer petioles (tables 11-13). This combined with poor bolting pressure suggests production of TBG 47 is best under conditions when fusarium becomes a significant production limiting stressor and especially when there is an increased risk for the presence of fusarium race 4. Currently this would be the Southern California production area in the fall to early winter and spring harvest seasons when warmer temperatures increase the infective potential for both fusarium race 2 and race 4.

Table 2 shows the result of a trial transplanted in Oxnard, California, Aug. 14, 2019, and evaluated Dec. 23, 2019 (131 days). This trial was grown in a production block that has been developed with especially high levels of *Fusarium oxysporum* race 4 levels in order to evaluate and develop varieties for increased tolerance to the disease. Not only is this field especially high in the disease, it is the location where the disease was first identified. The plant population (58,080 plants to the acre) was higher than the commercial norm of approximately 45,000 to 47,000 plants to the acre. TBG 47 was compared to TBG 27, 30, 52, and ADS-17, 21, and 26. NA (not available) represents data that was not able to be collected due to severe impact due to fusarium.

TABLE 2

| | | TBG 47 | TBG 52 | ADS-17 | TBG 27 | ADS-21 | TBG 30 | ADS-26 |
|---|---|---|---|---|---|---|---|---|
| Plant Height (cm) | Average | 75.3 | NA | NA | NA | NA | NA | NA |
| | Range | (0-100) | | | | | | |
| Whole Plant weight (kg) | Average | 1.3 | NA | NA | NA | NA | NA | NA |
| | Range | (0.76-1.88) | | | | | | |
| Trimmed Plant Weight (kg) | Average | 0.96 | NA | NA | NA | NA | NA | NA |
| | Range | (0-1.66) | | | | | | |
| Length of Outer Petioles to the joint (cm) | Average | 37.6 | NA | NA | NA | NA | NA | NA |
| | Range | (0-45.2) | | | | | | |
| % Survival | | 83% | 6% | 32% | 12% | 44% | 32% | 33% |
| % Marketable | | 80% | 0% | 0% | 0% | 0% | 0% | 0% |

Under the fusarium race 4 conditions of this trial, most varieties had few to several plants there were still alive but nearly dead at evaluation and were not able to sustain development of marketable celery stalks. However, TBG 47 demonstrated substantial tolerance. Each of the other extra tall petiole varieties present showed low survival percentages and no market potential.

Table 3 shows the result of a trial transplanted in Oxnard, California, Aug. 19, 2020, and evaluated Dec. 4, 2020 (107 days). This trial was grown in a production block that has been developed with especially high levels of *Fusarium oxysporum* race 4 levels in order to evaluate and develop varieties for increased tolerance to the disease. Not only is this field especially high in the disease, it is the location where the disease was first identified. The plant population (58,080 plants to the acre) was higher than the commercial norm of approximately 45,000 to 47,000 plants to the acre.

TABLE 3

| | | TBG 47 | TBG 52 | TBG 44 | TBG 27 | ADS-17 | ADS-21 | TBG 30 |
|---|---|---|---|---|---|---|---|---|
| Plant Height (cm) | Average | 78.5 | 3.4 | 0 | 0.7 | 0.4 | 0.8 | 0 |
| | Range | (74-84) | (0-40) | (0-0) | (0-14) | (0-10) | (0-9) | (0-0) |
| Whole Plant Weight (kg) | Average | 0.79 | NA | NA | NA | NA | NA | NA |
| | Range | (0.47-0.97) | | | | | | |
| Weight 4-inch sticks (kg) | Average | 0.33 | NA | NA | NA | NA | NA | NA |
| | Range | (0.2-0.4) | | | | | | |
| | Range | | (0.2-0.4) | | | | | |
| Petiole Smoothness | | Smooth/Slight Rib | NA | NA | NA | NA | NA | NA |
| Petiole Cup | | Cup | NA | NA | NA | NA | NA | NA |
| % Marketable | | 95% | 0% | 0% | 0% | 0% | 0% | 0% |
| Disease: | | | | | | | | |
| Survival Rate (%) | Healthy | 100% | 7% | 0% | 0% | 0% | 0% | 0% |
| | Dying | 0% | 8% | 0% | 5% | 5% | 10% | 0% |
| | Dead | 0% | 85% | 100% | 95% | 95% | 90% | 100% |
| Overall Fusarium Ratings | Average | 4.5 | 0 | 0 | 0 | 0 | 0 | 0 |
| [0 to 5 (0 = dead, 5 = tolerant)] | Range | 4-5 | (0-2) | (0-0) | (0-1) | (0-1) | (0-1) | (0-1) |

As shown in Table 3, under the fusarium conditions of this trial, the varieties TBG 52, TBG 44, TBG 27, ADS-17, ADS 21, and TBG 30 were very susceptible. No varieties were able to produce marketable celery, and most were either dying or had died. TBG 47 was comparatively tolerant with 100% survival and an overall fusarium rating of 4.5.

Table 4 shows the result of a trial transplanted in Oxnard, California Apr. 17, 2020, and evaluated Jul. 7, 2020 (81 days). This trial was grown in a production block that has been developed with especially high levels of *Fusarium oxysporum* race 4 in order to evaluate and develop varieties for increased tolerance to the disease. Not only is this field especially high in the disease it is the location where the disease was first identified. The plant population (58,080 plants to the acre) was higher than the commercial norm of approximately 45,000 to 47,000 plants to the acre. In order to increase the impact of the disease in the spring, this trial was transplanted late in the season when the soil temperature (active temperature for the disease) was higher, and the celery was not able to reach full maturity due to a mandated celery free window in Ventura County. Some data was not collected for varieties that were 0% marketable and was noted by NA (not available).

TABLE 4

| | | TBG 47 | TBG 52 | ADS-17 | TBG 30 | ADS-26 |
|---|---|---|---|---|---|---|
| Plant Height (cm) | Average | 35.4 | 2.7 | NA | NA | 3.4 |
| | Range | (0-64) | (0-27) | | | (0-34) |
| Number of Outer Petioles (>35.6 cm) | Average | 5.2 | NA | NA | NA | NA |
| | Range | (0-10) | | | | |
| Number of Inner Petioles (<35.6 cm) | Average | 2.1 | NA | NA | NA | NA |
| | Range | (0-4) | | | | |
| Length of Outer Petioles to the joint (cm) | Average | 17.6 | 1.0 | NA | NA | 1.4 |
| | Range | (0-32.3) | (0-10.3) | | | (0-14) |
| % Survival | | 60% | 3% | 0% | 0% | 9% |
| % Marketable | | 60% | 0% | 0% | 0% | 0% |

As shown in Table 4, under the fusarium race 4 conditions of this trial TBG 47, TBG 52, and ADS-26 each had plants that survived, but only TBG 47 showed tolerance levels sufficient to produce plants with market potential.

Table 5 shows the result of a trial transplanted in Oxnard, California Aug. 17, 2021, and evaluated Nov. 22, 2021 (97 days) in a block that had especially high levels of *Fusarium oxysporum* f. sp. *apii* race 2 and slight to moderate levels from *Fusarium oxysporum* f. sp. *apii* race 4. The plant population (58,080 plants to the acre) was higher than the commercial norm of approximately 45,000 to 47,000 plants to the acre. TBG 47 was compared to TBG 30, 52, 54, ADS-17, 26 and Stix. For varieties that had no marketable stalks, except for joint length on some and fusarium ratings, no data was collected and represented by NA (not available).

TABLE 5

| | | TBG 47 | TBG 52 | ADS-26 | ADS-17 | TBG 30 | TBG 54 | STIX |
|---|---|---|---|---|---|---|---|---|
| Plant Height (cm) | Average | 92.4 | 82.9 | 92.3 | NA | NA | NA | 83.0 |
| | Range | (86-99) | (61-101) | (83-101) | | | | (68-102) |
| Whole Plant weight (kg) | Average | 0.95 | 0.93 | 0.78 | NA | NA | NA | 1.22 |
| | Range | (0.5-1.46) | (0.31-1.67) | (0.48-0.99) | | | | (0.49-2.44) |
| Trimmed Plant Weight (kg @ 35.6 cm) | Average | 0.86 | 0.87 | 0.71 | NA | NA | NA | 1.12 |
| | Range | (0.5-1.32) | (0.33-1.59) | (0.45-0.88) | | | | (0.47-2.16) |
| Number of Outer Petioles (>35.6 cm) | Average | 7.5 | 3.6 | 6.9 | NA | NA | NA | 2.4 |
| | Range | (6-10) | (0-8) | (4-8) | | | | (0-7) |
| Number of Inner Petioles (<35.6 cm) | Average | 7.5 | 11 | 4.9 | NA | NA | NA | 16.1 |
| | Range | (4-11) | (6-16) | (2-9) | | | | (8-23) |
| Length of Outer Petioles to the joint (cm) | Average | 44.3 | 39.5 | 47.3 | NA | 3.1 | 3.0 | 34.6 |
| | Range | (37-49.3) | (30-45) | (40.7-50.7) | | (1.7-4) | (1.7-4.7) | (26.3-41.3) |
| Width of Outer Petioles at the midrib (mm) | Average | 15.7 | 15.0 | 14.8 | NA | NA | NA | 18.0 |
| | Range | (11.8-19.6) | (8-20.1) | (11.2-17.6) | | | | (14.2-22.4) |

TABLE 5-continued

| | | TBG 47 | TBG 52 | ADS-26 | ADS-17 | TBG 30 | TBG 54 | STIX |
|---|---|---|---|---|---|---|---|---|
| Thickness of Outer Petioles at the midrib (mm) | Average | 8.2 | 8.1 | 8.6 | NA | NA | NA | 9.9 |
| | Range | (6.5-9.5) | (5.7-9.6) | (6.4-9.7) | | | | (7.8-12.6) |
| Number 4-inch Sticks | Average | 25.3 | 23.1 | 26.3 | NA | NA | NA | 25.1 |
| | Range | (22-30) | (9-32) | (21-33) | | | | (14-46) |
| Weight 4-inch Sticks (kg) | Average | 0.38 | 0.35 | 0.36 | NA | NA | NA | 0.38 |
| | Range | (0.22-0.5) | (0.08-0.61) | (0.26-0.48) | | | | (0.12-0.85) |
| Petiole Color (Munsell Color Chart) | | 7.5GY 7/8 | 7.5GY 7/6 | 7.5GY 8/6 | NA | NA | NA | 5GY 6/6 |
| Leaf Color (Munsell Color Chart) | | 5GY 4/4 | 7.5GY 4/4 | 7.5GY 4/4 | NA | NA | NA | 5GY 4/6 |
| Petiole Smoothness | | Slight Rib/Rib | Slight Rib | Ribby | NA | NA | NA | Slight Rib |
| Petiole Cup | | Cup | Cup | Cup | NA | NA | NA | Cup/Deep Cup |
| % Marketable | | 60% | 30% | 60% | 0% | 0% | 0% | 20% |
| Disease: | | | | | | | | |
| Root Fusarium Ratings [0 to 5 (0 = dead, 5 = tolerant)] | Average | 4.7 | 2 | 2.5 | 0 | 1 | 1 | 1.3 |
| | Range | (4-5) | (1-2) | (1-5) | (0) | (1) | (1-2) | (1-2) |

Under the conditions shown in Table 5, TBG 47 had the best fusarium ratings due to its tolerance to both fusarium race 2 and race 4. TBG 52 and ADS-26 which have levels of tolerance to race 2 were poorer but improved compared to ADS-17, TBG 30, TBG 54, and Stix. Percentage of marketable stalks for TBG 52 and Stix were lower than TBG 47 and ADS-26 yet the yield for four-inch sticks (number and weight) was only slightly lower to similar.

Table 6 shows the result of a trial transplanted in Oxnard, California, Aug. 6, 2020, and evaluated Oct. 30, 2020 (85 days). This trial was grown in a production block that has fairly high levels of *Fusarium oxysporum* race 2. Under these conditions we were able to evaluate varieties for relative tolerance to the disease. The plant population (58, 080 plants to the acre) was higher than the commercial norm of approximately 45,000 to 47,000 plants to the acre. Except for plant height, length of outer petioles, and fusarium ratings data was not collected for varieties were 0% marketable and is noted as NA (not available).

TABLE 6

| | | TBG 47 | TBG 52 | TBG 44 | TBG 27 | ADS-17 | ADS-21 | TBG 30 | STIX |
|---|---|---|---|---|---|---|---|---|---|
| Plant Height (cm) | Average | 90.4 | 95.1 | 18.8 | 21.3 | 26.2 | 43.1 | 46.1 | 94.8 |
| | Range | (85-96) | (79-103) | (0-40) | (0-49) | (0-54) | (0-74) | (0-70) | (82-104) |
| Trimmed Plant Weight (kg @ 35.6 cm) | Average | 1.15 | 1.03 | NA | NA | NA | NA | NA | 0.88 |
| | Range | (0.92-1.35) | (0.7-1.43) | | | | | | (0.36-1.35) |
| Number of Outer Petioles (>35.6 cm) | Average | 12.4 | 11.9 | NA | NA | NA | NA | NA | 9.6 |
| | Range | (10-15) | (9-15) | | | | | | (7-13) |
| Number of Inner Petioles (<35.6 cm) | Average | 3.0 | 3.5 | NA | NA | NA | NA | NA | 4.3 |
| | Range | (2-4) | (3-4) | | | | | | (3-5) |
| Length of Outer Petioles @ joint (cm) | Average | 43.8 | 45.1 | 8.6 | 11.9 | 13.7 | 18.1 | 19.8 | 41.0 |
| | Range | (41.7-46.3) | (36.7-50) | (0-19) | (0-28.3) | (0-28.7) | (0-28.3) | (0-28.3) | (33.3-48) |
| Width of Outer Petioles @ midrib (mm) | Average | 17.9 | 18.1 | NA | NA | NA | NA | NA | 15.6 |
| | Range | (16.3-19) | (17-20) | | | | | | (7-19.3) |
| Thickness of Outer Petioles midrib (mm) | Average | 9.6 | 10.1 | NA | NA | NA | NA | NA | 8.9 |
| | Range | (8.7-11) | (8.7-12.3) | | | | | | (6.7-10) |
| Number 4-inch Sticks | Average | 34.5 | 32.8 | NA | NA | NA | NA | NA | 21.6 |
| | Range | (29-39) | (19-45) | | | | | | (8-28) |
| Weight 4-inch Sticks (kg) | Average | 0.52 | 0.51 | NA | NA | NA | NA | NA | 0.36 |
| | Range | (0.42-0.67) | (0.26-0.73) | | | | | | (0.08-0.61) |
| Petiole Color (Munsell Color Chart) | | 5gy 7/6 | 5gy 6/6 | NA | NA | NA | NA | NA | 5gy 6/6 |
| Leaf Color (Munsell Color Chart) | | 5gy 4/4 | 5gy 4/4 | NA | NA | NA | NA | NA | 5gy 4/4 |
| Petiole Smoothness | | Smooth | Slight Rib | NA | NA | NA | NA | NA | Slight Rib/Rib |
| Petiole Cup | | Cup | Cup | NA | NA | NA | NA | NA | Cup |
| % Marketable | | 100% | 100% | 0% | 0% | 0% | 0% | 0% | 20% |
| Overall Fusarium Ratings [1 to 5 (1 = susceptible, 5 = tolerant)] | Average | 5 | 4.5 | 1 | 1 | 1 | 2 | 2.5 | 3.5 |
| | Range | 5 | 3.5 | 0-1 | 0-2 | 0-2 | 0-3 | 0-3 | 3-5 |
| Root Fusarium Ratings [1 to 5 (1 = susceptible, 5 = tolerant)] | Average | 5 | 4.5 | 1 | 1 | 1 | 1 | 1.5 | 3 |
| | Range | 5 | 2.5 | 0-1 | 0-3 | 0-2 | 0-2 | 0-3 | 1-5 |

Under the *Fusarium oxysporum* race 2 conditions present in this trial, TBG 47 was the most consistently tolerant variety (overall and root fusarium ratings). TBG 52 outperformed TBG 47 for plant height, length of outer petioles and yield based on weight of 4-inch sticks. TBG 47 performed better for trimmed plant weight, number of outer petioles, and number of 4-inch sticks.

Table 7 shows the result of a trial transplanted in Oxnard, California Mar. 17, 2021, and evaluated Jun. 26, 2021 (101 days). This trial was grown in a production block that has been developed with especially high levels of *Fusarium oxysporum* race 2 in order to evaluate and develop varieties for increased tolerance to the disease. The celery in this trial was also exposed to slight pressure for bolting (327 hours below 50° F.). The plant population (58,080 plants to the acre) was higher than the commercial norm of approximately 45,000 to 47,000 plants to the acre. TBG 47 was compared to TBG 52, TBG 30, ADS-26, TBG 27, ADS-17, and Stix. For varieties that had no marketable stalks, much of the data was not collected and depicted by NA (not available).

TABLE 7

| | | TBG 47 | TBG 52 | TBG 30 | ADS-26 | TBG 27 | ADS-17 | STIX |
|---|---|---|---|---|---|---|---|---|
| Plant Height (cm) | Average | 90.8 | 93.3 | 36.5 | 92.3 | 7.2 | 11.8 | NA |
| | Range | (82-96) | (87-101) | (0-60) | (11-112) | (0-25) | (0-31) | |
| Whole Plant Weight (kg) | Average | 1.12 | 1.24 | NA | 1.28 | NA | NA | NA |
| | Range | (0.86-1.4) | (0.76-1.52) | | (1-1.74) | | | |
| Trimmed Plant Weight (kg @ 35.6 cm) | Average | 1.03 | 0.74 | NA | 1.10 | NA | NA | NA |
| | Range | (0.8-1.28) | (0-1.32) | | (0.9-1.44) | | | |
| Number of Outer Petioles (>35.6 cm) | Average | 14.4 | 8.9 | NA | 14.3 | NA | NA | NA |
| | Range | (13-16) | (0-15) | | (11-18) | | | |
| Number of Inner Petioles (<35.6 cm) | Average | 5.1 | 3.4 | NA | 3.2 | NA | NA | NA |
| | Range | (4-6) | (0-7) | | (2-4) | | | |
| Length of Outer Petioles @ joint (cm) | Average | 40.30 | 47.80 | NA | 49.13 | NA | NA | NA |
| | Range | (34.7-44.3) | (44-52) | | (38.7-55.7) | | | |
| Width of Outer Petioles @ midrib (mm) | Average | 18.93 | 14.30 | NA | 17.67 | NA | NA | NA |
| | Range | (16-22.7) | (0-23) | | (15.3-19.3) | | | |
| Thickness of Outer Petioles @ midrib (mm) | Average | 11.03 | 6.27 | NA | 8.33 | NA | NA | NA |
| | Range | (7.3-37) | (0-10) | | (7.3-9.7) | | | |
| Number 4-inch Sticks | Average | 38.2 | 26.9 | NA | 44.3 | NA | NA | NA |
| | Range | (29-45) | (0-43) | | (40-52) | | | |
| Weight 4-inch Sticks (kg) | Average | 0.5 | 0.41 | NA | 0.621 | NA | NA | NA |
| | Range | (0.32-0.62) | (0-0.74) | | (0.48-0.86) | | | |
| Seed Stem Length (cm) | Average | 0.1 | 12.8 | NA | 1.8 | NA | NA | 140.3 |
| | Range | (0-1) | (0-29) | | (0-18) | | | (120-150) |
| | Median | 0 | 9.0 | | 0 | | | 146.5 |
| Petiole Color (Munsell Color Chart) | | 5gy 6/6 | 5gy 6/6 | NA | 5gy 6/6 | NA | NA | NA |
| Leaf Color (Munsell Color Chart) | | 5gy 3/4 | 5 gy 3/4 | NA | 5gy 4/4 | NA | NA | NA |
| Petiole Smoothness | | Smooth/ Slight Rib | Smooth/ Slight Rib | NA | Smooth | NA | NA | NA |
| Petiole Cup | | Slight Cup/Cup | Cup | NA | Cup | NA | NA | NA |
| % Marketable | | 100% | 20% | 0% | 100% | 0% | 0% | 0% |
| Root Fusarium Ratings | Average | 5 | 4 | 1 | 5 | 0 | 0.5 | 2 |
| [1 to 5 (1 = susceptible, 5 = tolerant)] | Range | 5 | 4-5 | 0-2 | 3-5 | 0-1 | 0-1 | 1-2.5 |
| Overall Fusarium Ratings | Average | 5 | 4.5 | 1.5 | 4.5 | 0 | 0.5 | 2 |
| [1 to 5 (1 = susceptible, 5 = tolerant)] | Range | 5 | 4-5 | 0-2 | 4-5 | 0-1 | 0-1 | 1-2.5 |
| % Brown Stem | | 0% | 50% | NA | 0% | NA | NA | NA |
| % Top Pith | | 0% | 70% | NA | 0% | NA | NA | NA |
| % Suckers | | 0% | 0% | NA | 10% | NA | NA | NA |
| % Feather Leaf | | 0% | 30% | NA | 10% | NA | NA | NA |

As shown in Table 7, under these trial conditions with higher levels of fusarium race 2 and slight bolting pressure, TBG 47 was the most consistently tolerant variety for fusarium (root and overall fusarium ratings) and had the least developed seed stem. However, TBG 26 still outperformed it for yield based on four-inch stick count and weight.

Table 8 shows the result of a trial transplanted in Oxnard, California, Mar. 8, 2021, and evaluated Jun. 15, 2021 (99 days), in a normal production field with very low pressure due to *Fusarium oxysporum* race 2 and slight pressure for bolting (442 hours below 50° F.). The plant population (58,080 plants to the acre) was higher than the commercial norm of approximately 45,000 to 47,000 plants to the acre. TBG 47 was compared to varieties with relatively strong bolting tolerance (ADS-21, TBG 30 and TBG 44), varieties with fair fusarium race 2 tolerance and slight bolting tolerance (TBG 52, TBG 27, and Stix). Much data was not collected on varieties with an average seed stem longer than 20 cm (Stix) and was marked as not available (NA).

TABLE 8

| | | TBG 47 | TBG 52 | TBG 44 | TBG 27 | ADS-21 | TBG 30 | STIX |
|---|---|---|---|---|---|---|---|---|
| Plant Height (cm) | Average | 92.8 | 113.6 | 91.1 | 94.7 | 108.6 | 102.0 | 107 |
| | Range | (87-97) | (107-121) | (47-105) | (68-111) | (104-114) | (83-114) | (70-116) |
| Whole Plant weight (kg) | Average | 1.15 | 1.60 | 1.00 | 0.61 | 1.41 | 1.06 | NA |
| | Range | (1.04-1.34) | (1.26-1.88) | (0.14-1.82) | (0-1.98) | (1.04-1.9) | (0-1.74) | |
| Trimmed Plant Weight (kg @ 35.6 cm) | Average | 1.05 | 1.37 | 0.66 | 0.52 | 1.18 | 0.90 | NA |
| | Range | (0.96-1.18) | (1.12-1.62) | (0-1.5) | (0-1.64) | (0.9-1.56) | (0-1.48) | |
| Number of Outer Petioles (>35.6 cm) | Average | 10.5 | 11.1 | 7.0 | 4.2 | 8.4 | 6.6 | NA |
| | Range | (8-12) | (9-12) | (2-9) | (0-11) | (7-10) | (0-10) | |
| Number of Inner Petioles (<35.6 cm) | Average | 3.6 | 3.5 | 2.2 | 2.2 | 3.3 | 2.1 | NA |
| | Range | (3-5) | (3-4) | (0-5) | (0-5) | (3-4) | (0-3) | |
| Length of Outer Petioles to the joint (cm) | Average | 46.0 | 57.9 | 43.6 | 47.8 | 54.1 | 48.0 | 40.7 |
| | Range | (43-48.7) | (52.7-62) | (20.3-52) | (22.3-62) | (48.3-57) | (38.3-53.3) | (28-51.7) |
| Width of Outer Petioles at the midrib (mm) | Average | 19.6 | 21.2 | 13.0 | 10.2 | 22.0 | 17.6 | NA |
| | Range | (18.7-21) | (19.7-22) | (0-25.3) | (0-22.3) | (19.7-24) | (0-24) | |
| Thickness of Outer Petioles at the midrib (mm) | Average | 9.2 | 9.7 | 6.2 | 5.3 | 10.5 | 9.0 | NA |
| | Range | (8.7-9.7) | (9-10.3) | (0-12.7) | (0-11) | (9.7-11.7) | (0-12.7) | |
| Number 4-inch Sticks | Average | 33.8 | 42.0 | 15.1 | 17.7 | 28.8 | 20.1 | NA |
| | Range | (27-39) | (32-48) | (0-30) | (0-52) | (25-34) | (0-30) | |
| Weight 4-inch Sticks (kg) | Average | 0.56 | 0.81 | 0.35 | 0.34 | 0.68 | 0.47 | NA |
| | Range | (0.5-0.62) | (0.64-0.96) | (0-0.84) | (0-1.08) | (0.5-0.92) | (0-0.76) | |
| Seed Stem Length (cm) | Average | 0.1 | 1.6 | 0.3 | 20.0 | 0.7 | 0.0 | 53.5 |
| | Range | (0-1) | (1-4) | (0-2) | (0.22-66) | (0-3) | (0-0) | (21-78) |
| | Median | 0 | 1.0 | 0.0 | 5.0 | 0.5 | 0.0 | 61.5 |
| Petiole Color (Munsell Color Chart) | | 5gy 6/6 | 5gy 7/6 | 2.5gy 7/6 | 5GY 7/6 | 5gy 7/6 | 5gy 7/6 | 5GY 7/6 |
| Leaf Color (Munsell Color Chart) | | 5gy 4/4 | 5gy 4/4 | 5gy 4/4 | 5gy 4/4 | 5gy 4/4 | 5gy 4/4 | 5gy 4/4 |
| Petiole Smoothness | | Smooth | Slight Rib/Rib | Slight Rib/Rib | Slight Rib | Slight Rib/Rib | Smooth/Slight Rib | Rib |
| Petiole Cup | | Cup | Cup | Cup | Cup | Cup | Cup/Deep Cup | Cup |
| Overall Fusarium Ratings [1 to 5 (1 = susceptible, 5 = tolerant)] | Average | 5 | 5 | 2 | 3.5 | 4.5 | 4 | 3.5 |
| | Range | 5 | 5 | 1-3 | 1-5 | 3-5 | 1-5 | 2-5 |
| Root Fusarium Ratings [1 to 5 (1 = susceptible, 5 = tolerant)] | Average | 5 | 5 | 1.5 | 1 | 4 | 3 | 3 |
| | Range | 5 | 5 | 1-3 | 1-2 | 3-5 | 1-4 | 1-5 |

As shown in Table 8, under these conditions TBG 47 was most similar to TBG 52 for fusarium tolerance (overall and root fusarium ratings). It also had lower seed stem development compared to TBG 52, ADS-27, and Stix. TBG 47 ranked in the top three for yield with TBG 52 and ADS-21 which performed better or similarly for four-inch stick count and weight.

Table 9 shows the result of a trial transplanted in Santa Paula, California, Jan. 7, 2022, and evaluated May 5, 2022 (118 days). This trial was grown in a normal production field that had strong pressure for bolting (798 hours below 50° F.). The only characteristics measured for varieties with an average seed stem length of 10 cm and higher was the seed stem length. The plant population (58,080 plants to the acre) was higher than the commercial norm of approximately 45,000 to 47,000 plants to the acre. In this trial TBG 47 was compared to TBG 52, TBG 30, TBG 44, ADS-26, ADS-17, TBG 27, and Stix.

TABLE 9

| | | TBG 47 | TBG 52 | TBG 30 | TBG 44 | ADS-26 | ADS-17 | TBG 27 | Stix |
|---|---|---|---|---|---|---|---|---|---|
| Plant Height (cm) | Average | NA | NA | 89.2 | 93.6 | 112.2 | NA | NA | NA |
| | Range | | | (80-95) | (86-99) | (107-117) | | | |
| Whole Plant Weight (kg) | Average | NA | NA | 0.95 | 12.73 | 1.07 | NA | NA | NA |
| | Range | | | (0.57-1.22) | (0.88-118) | (0.57-1.4) | | | |
| Trimmed Plant Weight (kg @ 35.6 cm) | Average | NA | NA | 0.86 | 0.98 | 0.906 | NA | NA | NA |
| | Range | | | (0.52-1.08) | (0.85-1.14) | (0.51-1.22) | | | |
| Number of Outer Petioles (>35.6 cm) | Average | NA | NA | 10.5 | 10.7 | 10.7 | NA | NA | NA |
| | Range | | | (9-13) | (5-14) | (7-13) | | | |
| Number of Inner Petioles (<35.6 cm) | Average | NA | NA | 6.4 | 5-7 | 3.7 | NA | NA | NA |
| | Range | | | (4-8) | (0-8) | (0-5) | | | |
| Length of Outer Petioles to the joint (cm) | Average | NA | NA | 50.9 | 55.6 | 58.1 | NA | NA | NA |
| | Range | | | (46-53) | (45.7-61.3) | (52.7-62.3) | | | |
| Width of Outer Petioles at the midrib (mm) | Average | NA | NA | 16.9 | 18.3 | 15.7 | NA | NA | NA |
| | Range | | | (14.1-18.6) | (15.9-19.6) | (13-18) | | | |
| Thickness of Outer Petioles at midrib (mm) | Average | NA | NA | 7.5 | 8.1 | 12.7 | NA | NA | NA |
| | Range | | | (5.9-9) | (6.5-8.8) | (10.5-14.6) | | | |
| Distance between $1^{st}$ to $2^{nd}$ joint (cm) | Average | NA | NA | 0.0 | 0.0 | 0.0 | NA | NA | NA |
| | Range | | | (0-0) | (0-0) | (0-0) | | | |
| Number 4-inch Sticks | Average | NA | NA | 33.3 | 36.1 | 40.6 | NA | NA | NA |
| | Range | | | (27-41) | (19-45) | (23-50) | | | |
| Weight 4-inch Sticks (kg) | Average | NA | NA | 0.51 | 0.567 | 0.56 | NA | NA | NA |
| | Range | | | (0.32-0.67) | (0.45-0.65) | (0.29-0.72) | | | |
| Seed Stem Length (cm) | Average | 59.1 | 39.0 | 0.1 | 1.71 | 2.8 | 79.7 | 66.9 | 78.8 |
| | Range | (12-147) | (15-71) | 0-0.6 | (0-17.1) | (0-18) | (53-93) | (43-86) | (43-109) |
| | Median | 55.5 | 41.5 | 0.0 | 0.0 | 0.4 | 83.5 | 67.0 | 86.0 |
| Petiole Color (Munsell Color Chart) | | NA | NA | 5GY 7/6 | 5GY 6/6 | 5GY 4/6 | NA | NA | NA |
| Leaf Color (Munsell Color Chart) | | NA | NA | 5GY 5/6 | 5GY 4/4 | 5GY 5/6 | NA | NA | NA |
| Petiole Smoothness | | NA | NA | Slight Rib | Slight Rib | Slight Rib | NA | NA | NA |
| Petiole Cup | | NA | NA | Cup | Cup | Cup | NA | NA | NA |
| % Marketable | | 0% | 0% | 100% | 100% | 100% | 0% | 0% | 0% |

Under these conditions with higher pressure for bolting TBG 47 did not perform well due to general susceptibility to bolting. While performing considerably poorer for bolting (seed stem length) compared to varieties with improved bolting tolerance (TBG 30, TBG 44, and ADS-26) it was slightly improved compared to ADS-17 and Stix.

Table 10 shows the results of a trial transplanted in in Oxnard, California, Aug. 19, 2019, and evaluated Dec. 13, 2019, (116 days) in a normal production field with no significant pressure from disease or environmental conditions. However, the trial was slightly over mature when trial evaluation took place. The plant population (58,080 plants to the acre) was higher than the commercial norm of approximately 45,000 to 47,000 plants to the acre. TBG 47 was compared to TBG 52, ADS-26, TBG 30, ADS-17, and Stix.

TABLE 10

| | | TBG 47 | TBG 52 | ADS-26 | TBG 30 | ADS-17 | STIX |
|---|---|---|---|---|---|---|---|
| Plant Height (cm) | Average | 107.0 | 106.2 | 99.8 | 99.8 | 103.00 | 102.2 |
| | Range | (107-107) | (102-109) | (92-104) | (86-108) | (97-107) | (92-117) |
| Trimmed Plant Weight (kg @ 35.6 cm) | Average | 1.21 | 1.22 | 0.81 | 0.93 | 1.10 | 0.93 |
| | Range | (0.98-1.54) | (1.02-1.5) | (0.6-1) | (0.6-1.24) | (0.68-1.46) | (0.7-1.42) |
| Number of Outer Petioles (>35.6 cm) | Average | 14.1 | 13.1 | 10.8 | 11.0 | 11.4 | 12.4 |
| | Range | (12-16) | (12-15) | (7-15) | (8-13) | (7-15) | (10-17) |
| Number of Inner Petioles (<35.6 cm) | Average | 3.2 | 3.3 | 3.1 | 3.0 | 2.8 | 4.2 |
| | Range | (3-4) | (3-4) | (3-4) | (3-3) | (2-3) | (3-5) |
| Length of Outer Petioles @ joint (cm) | Average | 50.0 | 49.2 | 49.6 | 50.1 | 59.7 | 48.3 |
| | Range | (43-52.3) | (45-52) | (40.7-55.7) | (44-55.7) | (50.7-66.3) | (38-56) |
| Width of Outer Petioles @ midrib (mm) | Average | 18.9 | 19.4 | 16.6 | 19.0 | 18.0 | 16.8 |
| | Range | (18-20.7) | (17.7-20.7) | (15-19) | (17.3-22) | (15-20) | (14.3-20.7) |
| Thickness of Outer Petioles @ midrib | Average | 9.7 | 9.9 | 8.9 | 10.0 | 10.0 | 8.9 |
| (mm) | Range | (9-10.7) | (9-10.7) | (7.3-10.3) | (8-11.3) | (8.7-10.7) | (7.7-11) |
| Number 4-inch Sticks | Average | 41.8 | 44.7 | 31.5 | 34.9 | 40.1 | 32.0 |
| | Range | (35-50) | (38-57) | (26-44) | (26-44) | (29-51) | (21-42) |
| Weight 4-inch Sticks (kg) | Average | 0.60 | 0.69 | 0.40 | 0.55 | 0.57 | 0.45 |
| | Range | (0.5-0.7) | (0.56-0.86) | (0.3-0.5) | (0.34-0.68) | (0.3-0.8) | (0.28-0.78) |
| Petiole Smoothness | | Smooth | Rib | Slight Rib/Rib | Rib | Smooth/ Slight Rib | Smooth/ Slight Rib |
| Petiole Cup | | Cup | Cup | Cup | Cup | Slight Cup/Cup | Cup |
| Marketable | | 100% | 100% | 100% | 100% | 100% | 100% |
| Defects: | | | | | | | |
| % Brown Stem | | 0% | 0% | 20% | 0% | 0% | 0% |
| % Top Pith | | 0% | 0% | 100% | 0% | 0% | 0% |
| % Twist | | 0% | 10% | 90% | 0% | 20% | 100% |

Under these production conditions, TBG 47 and TBG 52 were most similar to one another for overall performance. TBG 47 and TBG 52 were similar for and had the best performance for plant height, trimmed plant weight, and petiole thickness. They were also similar for length of outer petioles though ADS-17 outperformed them. TBG 52 performed better for petiole width and had the highest yield of all varieties (weight and number of 4-inch sticks) with TBG 47 being the second-best performer.

Table 11 shows the results of a trial transplanted in Oxnard, California, Aug. 31, 2021, and evaluated Dec. 7, 2021 (98 days), in a normal production field with no significant pressure from disease of environmental conditions. However, the trial was slightly over mature when trial evaluation took place. The plant population (58,080 plants to the acre) was higher than the commercial norm of approximately 45,000 to 47,000 plants to the acre. TBG 47 was compared to TBG 52, ADS-26, ADS-17, TBG 27, TBG 30, TBG 44, and Stix.

TABLE 11

| | | TBG 47 | TBG 52 | ADS-26 | ADS-17 | TBG 27 | TBG 30 | TBG 44 | STIX |
|---|---|---|---|---|---|---|---|---|---|
| Plant Height (cm) | Average | 103.9 | 92.4 | 117.4 | 102.0 | 106.0 | 104.7 | 103.4 | 106.2 |
| | Range | (97-114) | (10-111) | (105-126) | (92-111) | (97-112) | (97-115) | (86-120) | (92-122) |
| Trimmed Plant Weight | Average | 0.96 | 1.32 | 1.19 | 1.15 | 1.39 | 0.90 | 1.20 | 1.21 |
| (kg @ 35.6 cm) | Range | (0.63-1.54) | (1.11-1.59) | (0.75-1.73) | (0.89-1.48) | (1.02-2.07) | (0.52-1.29) | (0.68-1.59) | (0.67-1.69) |
| Number of Outer Petioles | Average | 6.7 | 14.7 | 8.6 | 8.4 | 8.8 | 6.2 | 7.4 | 6.8 |
| (>35.6 cm) | Range | (5-8) | (6-70) | (7-10) | (6-10) | (7-10) | (5-8) | (5-12) | (4-9) |
| Number of Inner Petioles | Average | 5.4 | 5.9 | 4.9 | 5.2 | 5.1 | 4.2 | 5.3 | 8.4 |
| (<35.6 cm) | Range | (2-9) | (5-8) | (3-7) | (4-7) | (4-7) | (3-7) | (4-8) | (7-11) |
| Length of Outer Petioles | Average | 46.7 | 51.7 | 59.7 | 55.6 | 61.9 | 54.9 | 55.1 | 49.9 |
| to the joint (cm) | Range | (43-51) | (46.3-59) | (55.7-67) | (45.7-63.7) | (53-67.3) | (49.7-58) | (46-68.3) | (38.7-59) |
| Width of Outer Petioles | Average | 17.2 | 19.4 | 21.0 | 18.6 | 19.3 | 18.2 | 19.3 | 18.9 |
| at the midrib (mm) | Range | (15.8-18.8) | (18.2-21.4) | (15.4-50) | (16.7-19.6) | (16.9-21.1) | (16.2-22.5) | (12.7-21.6) | (15.6-22.6) |
| Thickness of Outer | Average | 8.7 | 9.6 | 9.2 | 9.8 | 10.5 | 9.9 | 13.2 | 9.7 |
| Petioles at the midrib (mm) | Range | (7.8-10.5) | (8.6-11.1) | (7.9-10.7) | (8.9-10.5) | (9.5-11.4) | (9-11.7) | (8.8-40.9) | (7.1-11.3) |
| Number 4 inch Sticks | Average | 23.1 | 34.1 | 35.4 | 34.1 | 40.7 | 26.3 | 33.3 | 26.3 |
| | Range | (16-28) | (25-43) | (31-40) | (23-44) | (33-47) | (19-34) | (21-62) | (16-37) |
| Weight 4 inch Sticks (kg) | Average | 0.45 | 0.75 | 0.67 | 0.66 | 0.86 | 0.54 | 0.66 | 0.60 |
| | Range | (0.28-0.68) | (0.55-0.98) | (0.42-1.03) | (0.45-0.88) | (0.63-1.14) | (0.28-0.79) | (0.38-1.04) | (0.26-0.85) |
| Petiole Color (Munsell Color Chart) | | 5GY 7/6 | 5GY 7/8 | 5GY 7/6 | 5GY 7/6 | 5GY 7/6 | 5GY 7/6 | 5GY 7/6 | 5GY 7/4 |
| Leaf Color (Munsell Color Chart) | | 5GY 4/6 | 5GY 4/6 | 5GY 4/6 | 7.5GY 3/4 | 5GY 4/6 | 5GY 4/6 | 5GY 4/6 | 5GY 4/6 |
| Petiole Smoothness | | Slight Rib/Rib | Slight Rib/Rib | Slight Rib | Slight Rib | Slight Rib | Slight Rib/Rib | Slight Rib | Slight Rib |
| Petiole Cup | | Cup | Cup | Cup | Cup | Cup | Cup | Cup | Cup |
| % Marketable | | 90% | 90% | 100% | 100% | 90% | 30% | 90% | 60% |
| Defects: | | | | | | | | | |
| % Top Pith | | 0% | 0% | 10% | 0% | 10% | 10% | 10% | 10% |
| % Butt Pith | | 0% | 30% | 50% | 0% | 10% | 50% | 20% | 0% |
| % Node Crack | | 10% | 10% | 10% | 0% | 10% | 0% | 0% | 0% |
| % Suckers | | 0% | 0% | 10% | 20% | 10% | 0% | 0% | 10% |
| % Feather Leaf | | 0% | 0% | 0% | 0% | 10% | 0% | 0% | 0% |
| % Brown Stem | | 0% | 0% | 0% | 0% | 0% | 30% | 0% | 0% |

Under these production conditions with little to no disease or environmental stress, TBG 47 does not favorably compare with most varieties for yield (four-inch stick count or weight), trimmed plant weight, petiole count and petiole length. However, TBG 47 was fairly free from defects compared to the other varieties.

Table 12 shows the results of a trial transplanted in Oxnard, California, Mar. 3, 2022, and evaluated Jun. 17, 2022 (106 days), in a normal production field with very low pressure due to *Fusarium oxysporum* f. sp. *apii* race 2, no pressure due to *Fusarium oxysporum* f. sp. *apii* race 4 and no bolting pressure. The plant population (58,080 plants to the acre) was higher than the commercial norm of approximately 45,000 to 47,000 plants to the acre. In this trial a very tall process class celery TBG 47 was compared with process class celery varieties TBG 52, ADS-26, ADS-17, TBG 30, and TBG 44.

TABLE 12

| | | TBG 47 | TBG 52 | ADS-26 | ADS-17 | TBG 30 | TBG 44 |
|---|---|---|---|---|---|---|---|
| Plant Height (cm) | Average | 103.5 | 112.3 | 114.6 | 108.0 | 108.4 | 108.3 |
| | Range | (96-108) | (109-118) | (103-119) | (100-118) | (101-115) | (103-119) |
| Trimmed Plant Weight (kg @ 35.6 cm) | Average | 1.33 | 1.49 | 1.36 | 1.56 | 1.08 | 1.27 |
| | Range | (0.96-1.78) | (1.37-1.7) | (1.19-1.91) | (1.23-2.21) | (0.76-1.38) | (0.8-1.58) |
| Number of Outer Petioles (>35.6 cm) | Average | 12.7 | 13.3 | 11.3 | 12.3 | 10.8 | 11.2 |
| | Range | (10-15) | (10-16) | (10-13) | (10-16) | (9-12) | (7-13) |
| Number of Inner Petioles (<35.6 cm) | Average | 6.5 | 5.6 | 3.8 | 5.0 | 4.0 | 4.0 |
| | Range | (5-8) | (4-9) | (3-5) | (3-6) | (3-5) | (2-6) |
| Length of Outer Petioles to the joint (cm) | Average | 46.1 | 59.3 | 55.8 | 64.2 | 56.3 | 54.7 |
| | Range | (42.3-53) | (56-64.3) | (53.7-59) | (57.3-73.3) | (51-61) | (52.3-56.3) |
| Width of Outer Petioles at the midrib (mm) | Average | 18.4 | 17.9 | 18.8 | 19.3 | 17.5 | 18.4 |
| | Range | (16.6-20.3) | (13.8-20.7) | (16.6-20.6) | (0-22) | (13.8-19.5) | (16.7-19.8) |
| Thickness of Outer Petioles at the midrib (mm) | Average | 9.1 | 9.0 | 9.6 | 9.2 | 9.5 | 12.9 |
| | Range | (8.1-10.3) | (6.9-10.3) | (8.3-10.8) | (0-11.4) | (7.3-10.7) | (8.7-38) |
| Number 4-inch Sticks | Average | 34.3 | 51.4 | 39.5 | 50.3 | 38.7 | 37.6 |
| | Range | (27-42) | (46-56) | (31-49) | (40-63) | (31-43) | (24-43) |
| Weight 4-inch Sticks (kg) | Average | 0.66 | 0.89 | 0.82 | 0.93 | 0.63 | 0.73 |
| | Range | (0.5-0.9) | (0.83-1.04) | (0.71-1.1) | (0.78-1.13) | (0.4-0.8) | (0.45-0.97) |
| Petiole Color (Munsell Color Chart) | | 5GY 6/6 | 5GY 7/8 | 5GY 7/8 | 5GY 7/8 | 5GY 6/6 | 5GY 7/8 |
| Leaf Color (Munsell Color Chart) | | 5GY 4/4 | 5GY 4/6 | 5GY 4/6 | 5GY 4/6 | 5GY 4/8 | 5GY 4/6 |
| Petiole Smoothness | | Slight Rib | Slight Rib | Slight Rib | Slight Rib | Slight Rib | Slight Rib |
| Petiole Cup | | Cup | Cup | Cup | Cup | Cup | Cup |

Under these trial conditions with little to no disease or environmental stress, TBG 47 does not favorably compare with most varieties for yield (four-inch stick count or weight), trimmed plant weight, petiole count and petiole length.

Table 13 shows the result of a trial transplanted in in Salinas, California May 13, 2020, and evaluated Aug. 14, 2020 (92 days). This trial was grown in a normal production field that had no disease or bolting pressure. The plant population (52,800 plants to the acre) was higher than the commercial norm of approximately 45,000 to 47,000 plants to the acre. TBG 47 was compared to TBG 52, TBG 52, ADS-17, TBG 27, and ADS-26.

TABLE 13

| | | TBG 47 | TBG 52 | ADS-17 | TBG 27 | ADS-26 |
|---|---|---|---|---|---|---|
| Plant Height (cm) | Average | 98.9 | 111.9 | 111.9 | 110.1 | 110.7 |
| | Range | (93-105) | (106-116) | (106-116) | (105-120) | (103-117) |
| Trimmed Plant Weight (kg @ 35.6 cm) | Average | 1.1 | 1.29 | 1.29 | 1.31 | 1.09 |
| | Range | (0.6-1.42) | (1-1.82) | (1-1.82) | (1.18-1.56) | (0.86-1.5) |
| Number of Outer Petioles (>35.6 cm) | Average | 8.9 | 9.2 | 9.2 | 10.0 | 9.3 |
| | Range | (5-11) | (8-10) | (8-10) | (8-12) | (8-12) |
| Number of Inner Petioles (<35.6 cm) | Average | 4.8 | 4.7 | 4.7 | 3.6 | 2.8 |
| | Range | (3-7) | (3-7) | (3-7) | (3-5) | (2-3) |
| Length of Outer Petioles to the joint (cm) | Average | 49.7 | 54.2 | 54.2 | 66.9 | 59.6 |
| | Range | (44.7-59) | (49-57) | (49-57) | (60.3-74.7) | (52.7-63.3) |
| Width of Outer Petioles at the midrib (mm) | Average | 19.1 | 22.5 | 22.5 | 20.1 | 18.0 |
| | Range | (16.7-21) | (19.7-26.3) | (19.7-26.3) | (18.7-22) | (17-20.3) |
| Thickness of Outer Petioles at the midrib (mm) | Average | 8.6 | 9.4 | 9.4 | 10.1 | 8.6 |
| | Range | (7.7-9.7) | (8.7-12.3) | (8.7-12.3) | (9.3-11.3) | (7.3-10) |
| Number 4-inch Sticks | Average | 31.7 | 43.2 | 43.2 | 50.4 | 39.9 |
| | Range | (20-41) | (36-47) | (36-47) | (42-60) | (29-52) |
| Weight 4-inch Sticks (kg) | Average | 0.48 | 0.78 | 0.78 | 0.86 | 0.64 |
| | Range | (0.28-0.68) | (0.6-1.1) | (0.6-1.1) | (0.74-1.1) | (0.42-0.88) |
| Petiole Color (Munsell Color Chart) | | 2.5GY 6/8 | 5GY 6/6 | 5GY 6/6 | 5GY 7/6 | 5GY 7/8 |
| Leaf Color (Munsell Color Chart) | | 5GY 5/6 | 5GY 4/4 | 5GY 4/4 | 5GY 4/4 | 5GY 4/6 |
| Petiole Smoothness | | Smooth | Smooth/ Slight Rib | Smooth/ Slight Rib | Smooth/ Slight Rib | Smooth |
| Petiole Cup | | Cup | Cup | Cup | Slight Cup/Cup | Cup |
| % Marketable | | 100% | 100% | 100% | 100% | 100% |

Under these conditions with little to no disease or environmental stress, TBG 47 does not favorably compare with most varieties for yield (four-inch stick count or weight), trimmed plant weight, petiole count and petiole length.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the celery cultivar seed of this invention has been with the American Type Culture Collection (ATCC), 10801 University Boulevard, Manassas, Va. 20110, under Accession No. PTA-127789, under the terms of the Budapest Treaty. Access to this deposit will be available during the pendency of this application to persons determined by the Commissioner of Patents and Trademarks to be entitled thereto under 37 CFR § 1.14 and 35 USC § 122. All restrictions imposed by the depositor on the availability to the public of the deposited material will be irrevocably removed upon the granting of the patent.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A seed, plant, or a plant part thereof, of celery cultivar designated TBG 47, wherein a representative sample of seed of said cultivar has been deposited under ATCC Accession No. PTA-127789.

2. A celery plant, or a plant part thereof, having all of the physiological and morphological characteristics of the celery plant of claim 1.

3. A tissue or cell culture produced from protoplasts or cells from the plant of claim 1, wherein said cells or protoplasts are produced from a plant part selected from the group consisting of leaf, callus, pollen, ovule, embryo, cotyledon, hypocotyl, meristematic cell, root, root tip, pistil, anther, flower, seed, shoot, stem, stalk, petiole, and sucker.

4. A celery plant regenerated from the tissue culture of claim 3, wherein said regenerated plant comprises all of the morphological and physiological characteristics of celery cultivar TBG 47.

5. A method of producing a celery seed, wherein the method comprises crossing the plant of claim 1 with a different celery plant and harvesting the resultant celery seed.

6. An $F_1$ celery seed produced by the method of claim 5.

7. An $F_1$ celery plant, or a plant part thereof, produced by growing said seed of claim 6.

8. A method of producing an herbicide resistant celery plant, wherein said method comprises introducing a gene conferring herbicide resistance into the plant of claim 1.

9. A herbicide resistant celery plant produced by the method of claim 8, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, benzonitrile protoporphyrinogen oxidase (PPO)-inhibitor herbicides, auxin herbicides, and broxynil, wherein said plant comprises said gene and otherwise comprises all of the physiological and morphological characteristics of celery cultivar TBG 47.

10. A method of producing a pest or insect resistant celery plant, wherein said method comprises introducing a gene conferring pest or insect resistance into the celery plant of claim 1.

11. A pest or insect resistant celery plant produced by the method of claim 10, wherein said plant comprises said gene and otherwise comprises all of the physiological and morphological characteristics of celery cultivar TBG 47.

12. The celery plant of claim 11, wherein the gene encodes a *Bacillus thuringiensis* (Bt) endotoxin.

13. A method of producing a disease resistant celery plant, wherein said method comprises introducing a gene into the celery plant of claim 1.

14. A disease resistant celery plant produced by the method of claim 13.

15. A method of producing a celery plant with modified fatty acid metabolism or modified carbohydrate metabolism comprising transforming the celery plant of claim 1 with a transgene encoding a protein selected from the group consisting of fructosyltransferase, levansucrase, α-amylase, invertase and starch branching enzyme or DNA encoding an antisense of stearyl-ACP desaturase.

16. A celery plant having modified fatty acid metabolism or modified carbohydrate metabolism produced by the method of claim 15.

17. A method for producing a male sterile celery plant, wherein said method comprises transforming the celery plant of claim 1 with a nucleic acid molecule that confers male sterility.

18. A male sterile celery plant produced by the method of claim 17.

19. A method of introducing a desired trait into celery cultivar TBG 47, wherein the method comprises:

(a) crossing a TBG 47 plant, wherein a representative sample of seed was deposited under ATCC Accession No. PTA-127789, with a plant of another celery cultivar that comprises a desired trait to produce progeny plants, wherein the desired trait is selected from the group consisting of improved nutritional quality, industrial usage, male sterility, herbicide resistance, insect resistance, modified seed yield, modified lodging resistance, modified iron-deficiency chlorosis and resistance to bacterial disease, fungal disease or viral disease;

(b) selecting one or more progeny plants that have the desired trait to produce selected progeny plants;

(c) backcrossing the selected progeny plants with the TBG 47 plants to produce backcross progeny plants;

(d) selecting for backcross progeny plants that have the desired trait; and (e) repeating steps (c) and (d) two or more times in succession to produce selected third or higher backcross progeny plants that comprise the desired trait.

20. A celery plant produced by the method of claim 19, wherein the plant has the desired trait and otherwise all of the physiological and morphological characteristics of celery cultivar TBG 47.

21. The celery plant of claim 20, wherein the desired trait is herbicide resistance and the resistance is conferred to a herbicide selected from the group consisting of imidazolinone, dicamba, cyclohexanedione, sulfonylurea, glyphosate, glufosinate, phenoxy proprionic acid, L-phosphinothricin, triazine, benzonitrile protoporphyrinogen oxidase (PPO)-inhibitor herbicides, auxin herbicides, and broxynil.

22. The celery plant of claim 20, wherein the desired trait is insect resistance and the insect resistance is conferred by a gene encoding a *Bacillus thuringiensis* endotoxin.

23. The celery plant of claim 20, wherein the desired trait is male sterility and the trait is conferred by a cytoplasmic nucleic acid molecule.

24. A method of producing a genetically modified celery plant, wherein the method comprises mutation, transformation, gene conversion, genome editing, RNA interference or gene silencing of the plant of claim 1.

* * * * *